US009833595B2

(12) United States Patent
Gonzalez

(10) Patent No.: US 9,833,595 B2
(45) Date of Patent: Dec. 5, 2017

(54) DUAL-LEVER BI-DIRECTIONAL HANDLE

(75) Inventor: Pablo A. Gonzalez, Pomona, CA (US)

(73) Assignee: Biosense Webster, Inc., Diamond Bar, CA (US)

(*) Notice: Subject to any disclaimer, the term of this patent is extended or adjusted under 35 U.S.C. 154(b) by 987 days.

(21) Appl. No.: 11/323,219

(22) Filed: Dec. 30, 2005

(65) Prior Publication Data
US 2007/0156116 A1 Jul. 5, 2007

(51) Int. Cl.
A61M 25/01 (2006.01)
A61B 1/005 (2006.01)
A61B 1/008 (2006.01)
A61B 18/14 (2006.01)
A61B 5/00 (2006.01)
A61B 17/00 (2006.01)
A61M 25/00 (2006.01)

(52) U.S. Cl.
CPC ......... A61M 25/0136 (2013.01); A61B 1/008 (2013.01); A61B 1/0052 (2013.01); A61B 18/1492 (2013.01); A61M 25/0147 (2013.01); A61B 5/6852 (2013.01); A61B 2017/003 (2013.01); A61M 25/0029 (2013.01); A61M 2025/004 (2013.01); A61M 2025/0037 (2013.01); A61M 2025/015 (2013.01); A61M 2025/0161 (2013.01)

(58) Field of Classification Search
CPC .......... A61M 25/0136; A61M 25/0147; A61B 1/008; A61B 1/0052
USPC ............ 604/528, 523, 95.01, 95.04; 600/146
See application file for complete search history.

(56) References Cited

U.S. PATENT DOCUMENTS

| | | | | |
|---|---|---|---|---|
| 5,185,004 A | * | 2/1993 | Lashinski | 604/95.04 |
| RE34,502 E | * | 1/1994 | Webster, Jr. | 607/125 |
| 5,364,351 A | * | 11/1994 | Heinzelman et al. | 604/95.04 |
| 5,391,199 A | | 2/1995 | Ben-Haim | |
| 5,409,453 A | * | 4/1995 | Lundquist et al. | 604/22 |
| 5,441,483 A | * | 8/1995 | Avitall | 604/95.05 |

(Continued)

FOREIGN PATENT DOCUMENTS

DE 199 33 278 A1 1/2001
EP 0 904 796 A2 3/1999
(Continued)

OTHER PUBLICATIONS

European Search Report dated Nov. 5, 2007 for Application No. EP 06 25 6630, 7 sheets.
(Continued)

Primary Examiner — Bradley Osinski
(74) Attorney, Agent, or Firm — Lewis Roca Rothgerber Christie LLP

(57) ABSTRACT

An improved bi-directional steerable catheter is provided. The catheter generally comprises a catheter body, tip section and control handle. The catheter further comprises first and second puller wires extending from the control handle, through the catheter body and into the tip section. The control handle has deflection means for each puller wire that include a gear, and a carrier to which the proximal end of a puller wire is anchored. The gear is rotatably coupled to a lever controlled by an operator and the gear engages the carrier such that rotation of the gear by the lever results in longitudinal movement of the carrier, which results in deflection of the tip section.

12 Claims, 23 Drawing Sheets

(56) References Cited

U.S. PATENT DOCUMENTS

| | | | |
|---|---|---|---|
| 5,443,489 A | 8/1995 | Ben-Haim | |
| 5,456,664 A * | 10/1995 | Heinzelman et al. | 604/528 |
| 5,480,422 A | 1/1996 | Ben-Haim | |
| 5,531,686 A * | 7/1996 | Lundquist et al. | 604/95.04 |
| 5,546,951 A | 8/1996 | Ben-Haim | |
| 5,558,091 A | 9/1996 | Acker et al. | |
| 5,568,809 A | 10/1996 | Ben-haim | |
| 5,666,970 A * | 9/1997 | Smith | 600/585 |
| 5,803,083 A * | 9/1998 | Buck et al. | 600/439 |
| 5,848,986 A * | 12/1998 | Lundquist et al. | 604/22 |
| 5,931,811 A * | 8/1999 | Haissaguerre et al. | 604/95.03 |
| 5,938,616 A * | 8/1999 | Eaton et al. | 600/463 |
| 5,944,690 A * | 8/1999 | Falwell et al. | 604/170.03 |
| 5,964,757 A * | 10/1999 | Ponzi | 606/45 |
| 6,024,739 A * | 2/2000 | Ponzi et al. | 606/15 |
| 6,027,473 A * | 2/2000 | Ponzi | 604/528 |
| 6,033,378 A * | 3/2000 | Lundquist et al. | 604/95.01 |
| 6,066,125 A * | 5/2000 | Webster, Jr. | 604/528 |
| 6,120,476 A * | 9/2000 | Fung et al. | 604/95.04 |
| 6,123,699 A * | 9/2000 | Webster, Jr. | 604/528 |
| 6,171,277 B1 * | 1/2001 | Ponzi | 604/95.04 |
| 6,183,463 B1 * | 2/2001 | Webster, Jr. | 604/528 |
| 6,198,974 B1 * | 3/2001 | Webster, Jr. | 607/122 |
| 6,203,507 B1 * | 3/2001 | Wadsworth et al. | 600/585 |
| 6,210,362 B1 * | 4/2001 | Ponzi | 604/95.01 |
| 6,210,407 B1 * | 4/2001 | Webster | 606/41 |
| 6,224,587 B1 * | 5/2001 | Gibson | 604/528 |
| 6,267,746 B1 * | 7/2001 | Bumbalough | 604/95.01 |
| 6,402,719 B1 * | 6/2002 | Ponzi et al. | 604/95.04 |
| 6,468,260 B1 * | 10/2002 | Bumbalough et al. | 604/523 |
| 6,500,167 B1 * | 12/2002 | Webster, Jr. | 604/528 |
| 6,551,302 B1 * | 4/2003 | Rosinko et al. | 604/505 |
| 6,554,794 B1 * | 4/2003 | Mueller et al. | 604/95.04 |
| 6,571,131 B1 * | 5/2003 | Nguyen | 607/122 |
| 6,602,242 B1 * | 8/2003 | Fung et al. | 604/528 |
| 6,663,588 B2 * | 12/2003 | DuBois | A61M 25/0147 604/95.01 |
| 6,728,563 B2 * | 4/2004 | Rashidi | 600/374 |
| 6,783,510 B1 * | 8/2004 | Gibson et al. | 604/95.01 |
| 6,783,521 B2 * | 8/2004 | Ponzi et al. | 604/527 |
| 6,829,497 B2 * | 12/2004 | Mogul | 600/374 |
| 6,913,594 B2 * | 7/2005 | Coleman et al. | 604/95.04 |
| 7,004,938 B2 * | 2/2006 | Ormsby et al. | 606/33 |
| 7,033,345 B2 * | 4/2006 | Lee et al. | 604/528 |
| 7,056,314 B1 * | 6/2006 | Florio et al. | 604/528 |
| 7,087,064 B1 * | 8/2006 | Hyde | 606/142 |
| 7,811,277 B2 * | 10/2010 | Boulais | A61B 1/0052 604/528 |
| 2002/0161353 A1 * | 10/2002 | Kortelling | 604/528 |
| 2003/0114832 A1 * | 6/2003 | Kohler et al. | 604/528 |
| 2003/0120259 A1 * | 6/2003 | Mickley | 604/528 |
| 2005/0277874 A1 * | 12/2005 | Selkee | 604/95.04 |

FOREIGN PATENT DOCUMENTS

| | | |
|---|---|---|
| EP | 1 348 374 A1 | 10/2003 |
| JP | 58-188424 | 11/1983 |
| JP | 2-206418 | 8/1990 |
| WO | WO 92/00696 | 1/1992 |
| WO | WO 95/02995 | 2/1995 |

OTHER PUBLICATIONS

English translation of JP Office action dated Nov. 1, 2011, issued in Application No. JP 2006-355032, 3 pages.

* cited by examiner

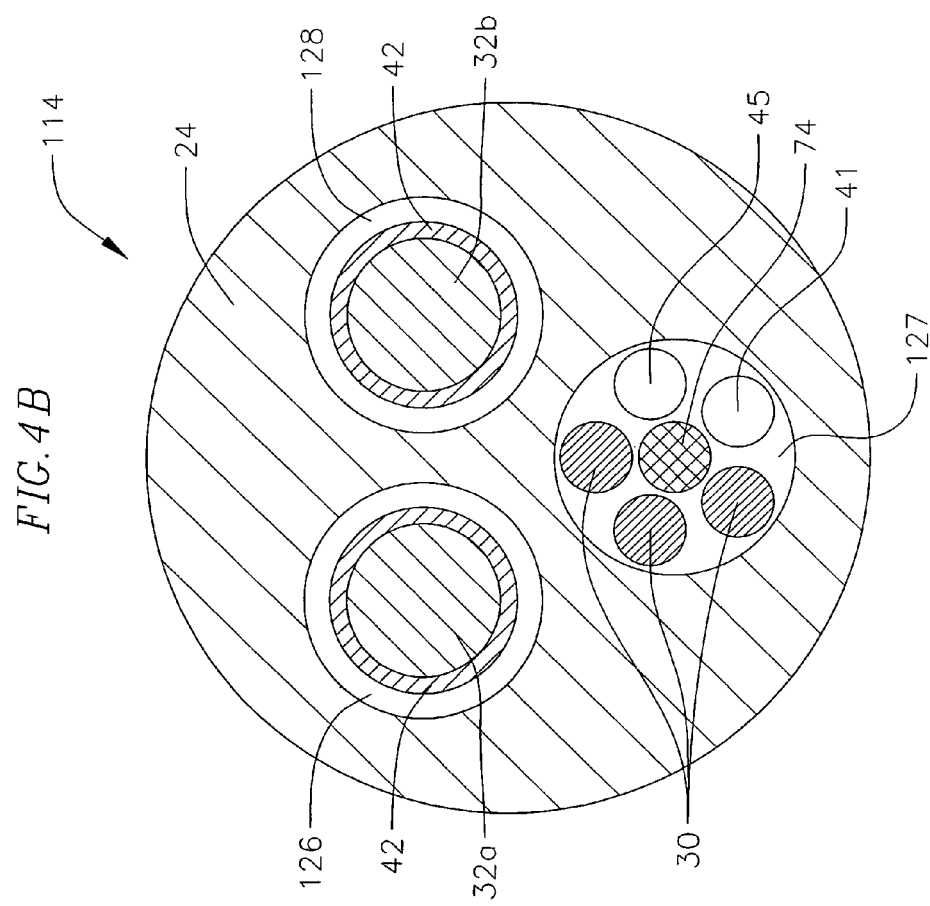

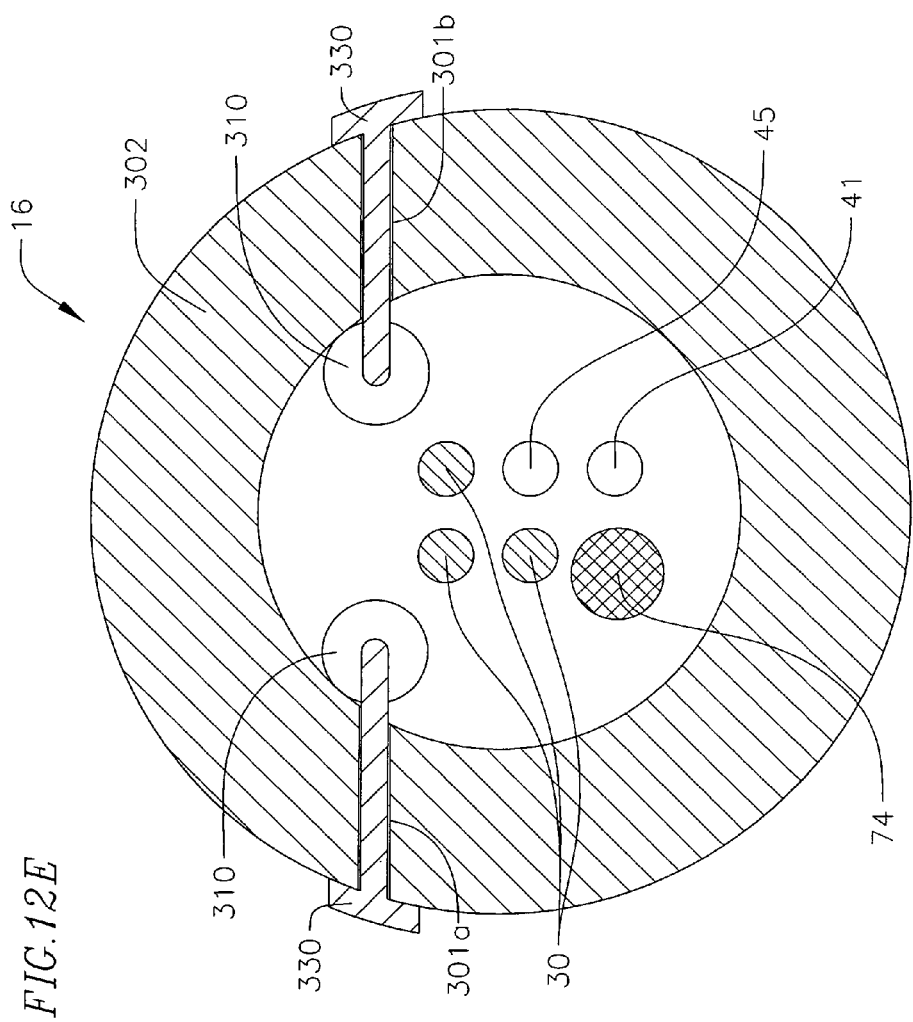

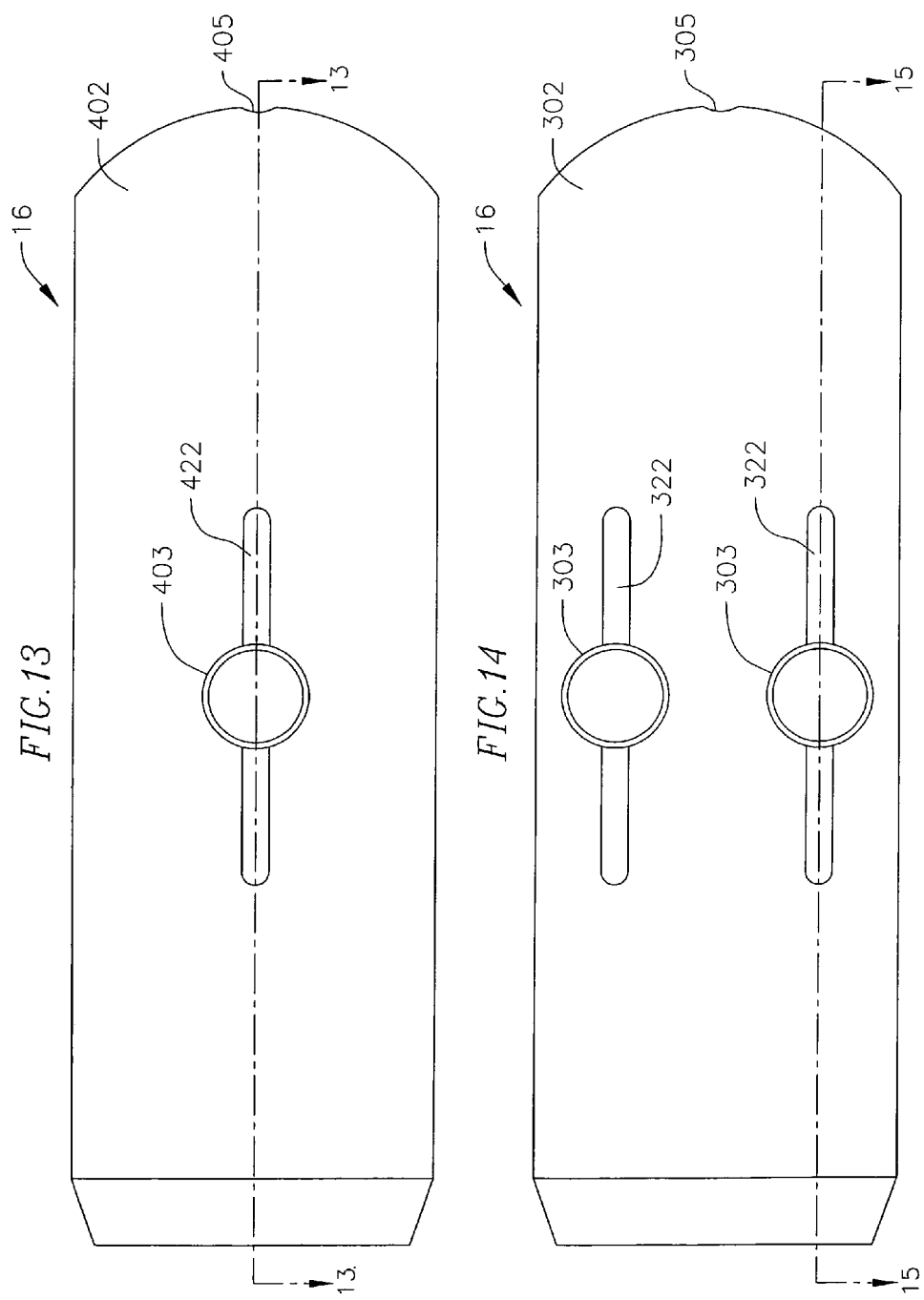

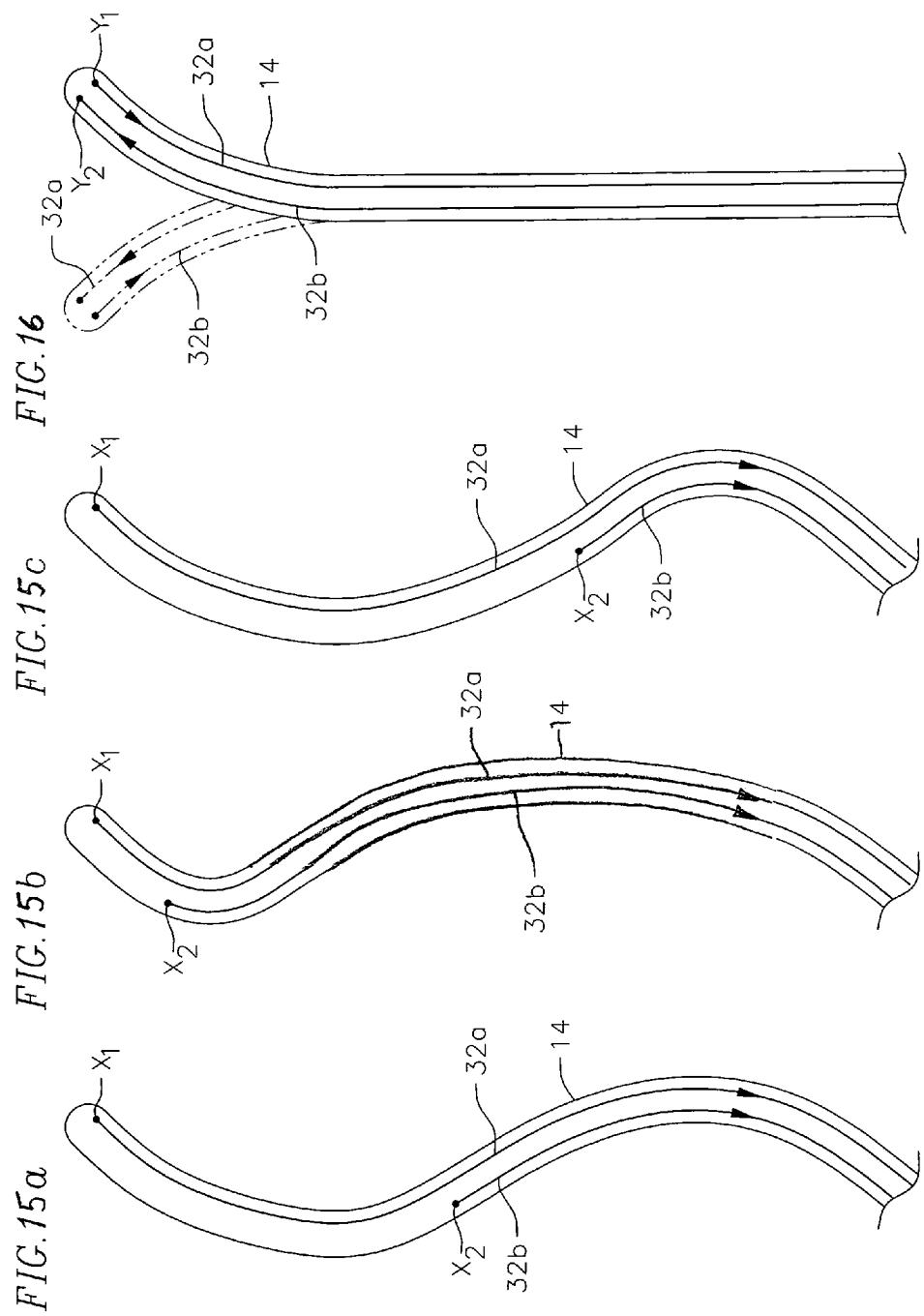

DUAL-LEVER BI-DIRECTIONAL HANDLE

FIELD OF THE INVENTION

The present invention relates to an improved bi-directional catheter and a control handle for the catheter.

BACKGROUND OF THE INVENTION

Electrode catheters have been in common use in medical practice for many years. They are used to stimulate and map electrical activity in the heart and to ablate sites of aberrant electrical activity.

In use, the electrode catheter is inserted into a major vein or artery, e.g. a femoral artery, and then guided into the chamber of the heart which is of concern. Within the heart, the ability to control the exact position and orientation of the catheter tip is critical, and largely determines the success of the catheter treatment.

Steerable (or deflectable) catheters are well-known. For example, a catheter having a control handle comprising a housing having a piston chamber at its distal end is described in U.S. Pat. No. RE 34,502, the entire content of which is incorporated herein by reference. In that control handle, a piston is mounted in the piston chamber and is afforded lengthwise movement. The proximal end of the catheter body is attached to the piston. A puller wire is attached to the housing and extends through the piston and through the catheter body. The distal end of the puller wire is anchored in the tip section of the catheter. In this arrangement, lengthwise movement of the piston relative to the housing results in deflection of the catheter tip section.

However, this design is generally limited to catheters having a single puller wire. Bi-directional catheters, i.e. catheters capable of deflecting in more than one direction without rotating the catheter body, require more than one puller wire. When two puller wires are used, it is undesirable for both wires to be moved simultaneously in the same direction. Therefore, the piston control handle design for single puller wire catheters is not well-suited for a two puller wire system, and a need exists for a control handle for a bi-directional catheter capable of independently moving the two puller wires and preventing simultaneous movement of the puller wires in the same direction.

SUMMARY OF THE INVENTION

The invention is directed to an improved bi-directional steerable catheter. In one embodiment, the catheter comprises an elongated, tubular catheter body having at least one lumen extending therethrough. A defectable tip section comprising flexible tubing having at least two lumens extending therethrough is fixedly attached to the distal end of the catheter body. The catheter further comprises first and second puller wires having proximal and distal ends. Each puller wire extends from the control handle, through the lumen in the catheter body and into an off-axis lumen in the tip section. The proximal ends of the puller wires are anchored within the control handle. The distal ends of the puller wires are anchored in the tip section.

The control handle is mounted at the proximal end of the catheter body and comprises a generally hollow handle housing. In one embodiment, the control handle has deflection means for each puller wire that include a gear, and a carrier to which the proximal end of the puller wire is anchored. For actuating a puller wire for deflection in its direction, an operator controls a lever that is rotatably coupled to the gear which is engaged with the carrier such that rotation of the gear by the lever results in longitudinal movement of the carrier, which results in deflection in the direction of the actuated puller wire. As such, the deflection means for each puller wire of a puller wire pair can operate generally independently of each other, where movement of one puller wire has minimal, if any, effect on the movement of the other puller wire.

In a more detailed embodiment, proximal movement of a lever relative to the handle housing causes rotational movement of the corresponding gear resulting in proximal movement of the corresponding carrier relative to the handle housing and catheter body, which results in deflection of the tip section in the direction of the lumen in which the corresponding puller wire extends. After deflection of the puller wire, distal movement of the corresponding lever relative to the handle housing results in distal movement of the corresponding carrier, which returns the puller wire to a straight or neutral configuration.

In an alternative embodiment, the movement of each puller wire can be coupled such that movement of one puller wire effects an opposite movement in the other puller wire. The control handle has deflection means comprising a single gear that is rotatably coupled to a single lever controlled by the operator and the gear engages both a first and a second carriers at generally opposing locations on a diameter of the gear. Proximal ends of a first puller wire and a second puller wire are anchored to the first and second carriers, respectively, and movement of the lever causes rotation of the gear resulting in generally equal but opposite movements of the first and second carriers, thereby deflecting the tip section in the direction of the puller wire drawn proximally and away from the direction of the puller wire advanced distally.

Moreover, in accordance with the present invention, depending on whether the distal ends of the puller wires are anchored in the tip section at the same distal length or at different distal lengths from the control handle, bi-directional deflection or "S" shape deflections are enabled by the deflection means. In one embodiment, the distal ends of both puller wire are anchored to the tip electrode. In another embodiment, the distal end of one puller wire is anchored more proximally than the distal end of the other puller wire. In particular, the distal end of one puller wire is anchored in the tip electrode and the distal end of the other puller wire is anchored more proximally in a side wall of the tip section.

BRIEF DESCRIPTION OF THE DRAWINGS

These and other features and advantages of the present invention will be better understood by reference to the following detailed description when considered in conjunction with the accompanying drawings; wherein:

FIG. 4B is a longitudinal cross-sectional view of the tip section of FIG. 4A taken along line 4B-4B;

FIG. 10b is a perspective view of a gear according to one embodiment of the present invention, suitable for use with the carrier of FIG. 10a;

FIG. 12E is a longitudinal cross-sectional view of the control handle of FIG. 12A taken along line 12C-12C;

FIG. 13 is a top view of a control handle according to another embodiment of the present invention;

FIG. 14 is a top view of a handle according to another embodiment of the present invention;

FIG. 15a is a perspective view of a catheter displaying a symmetrical "S" shape deflection;

FIG. 15b is a perspective view of a catheter displaying an asymmetrical "S" shape deflection;

FIG. 15c is a perspective view of a catheter displaying another asymmetrical "S" shape deflection;

FIG. 16 is a perspective view of a catheter displaying symmetrical bi-directional deflection.

DETAILED DESCRIPTION OF THE INVENTION

Figure 1:
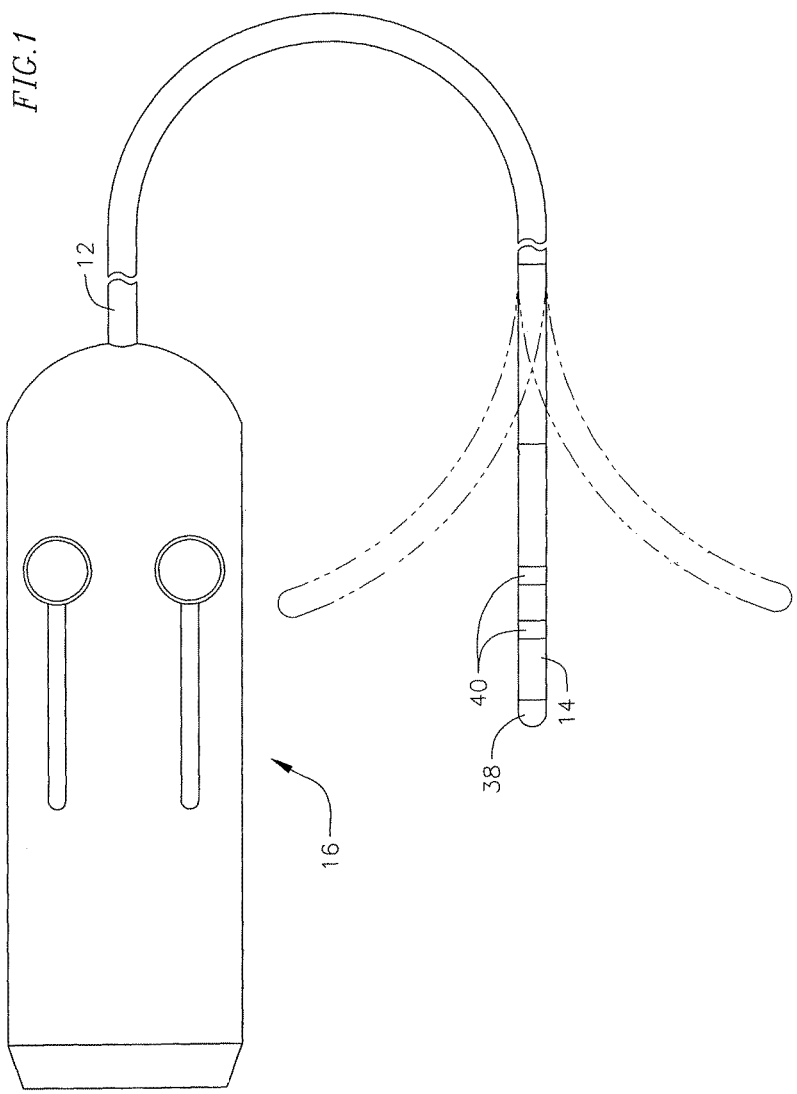
FIG. 1 is a top view of a catheter according to one embodiment of the present invention.

In one embodiment of the present invention, as shown in FIG. 1, a steerable (or deflectable) bi-directional catheter 10 comprises an elongated catheter body 12 having proximal and distal ends, a deflectable tip section 14 at the distal end of the catheter body 12, and a control handle 16 at the proximal end of the catheter body 12.

Figure 2:
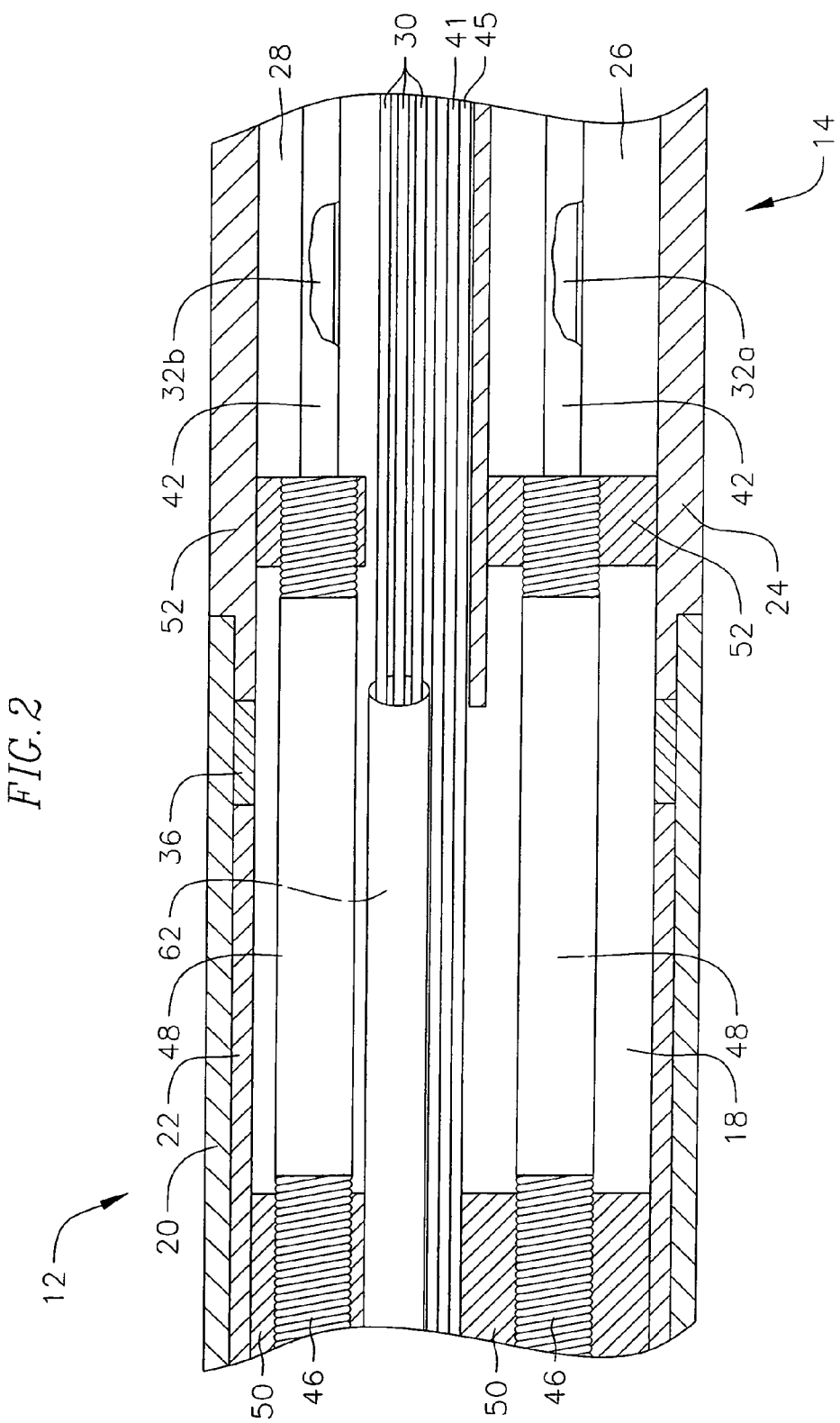
FIG. 2 is a side cross-sectional view of a catheter body according to one embodiment of the present invention, including the junction between the catheter body and tip section.
Figure 3A:
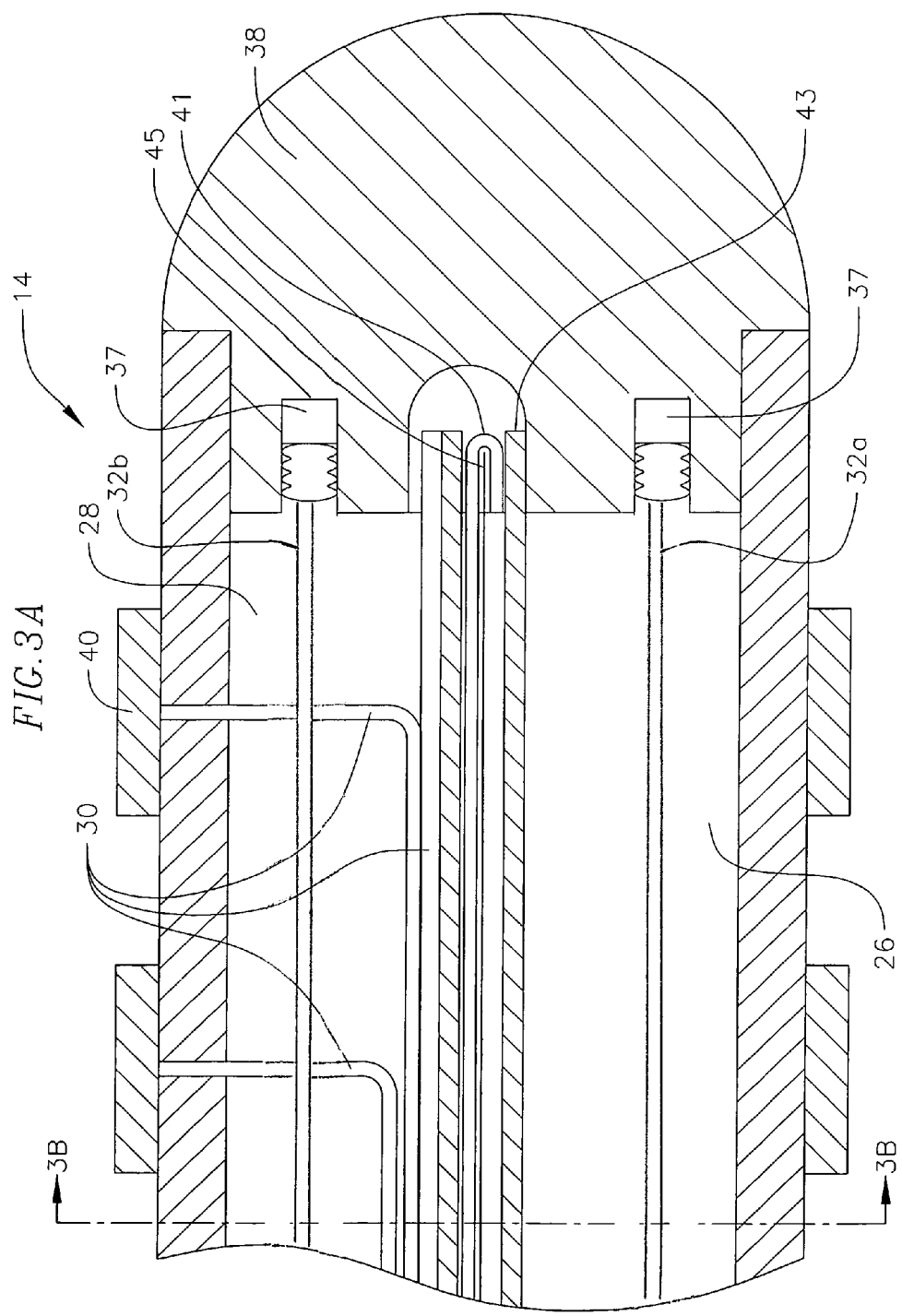
FIG. 3A is a side cross-sectional view of a tip section according to one embodiment of the present invention.
Figure 3B:
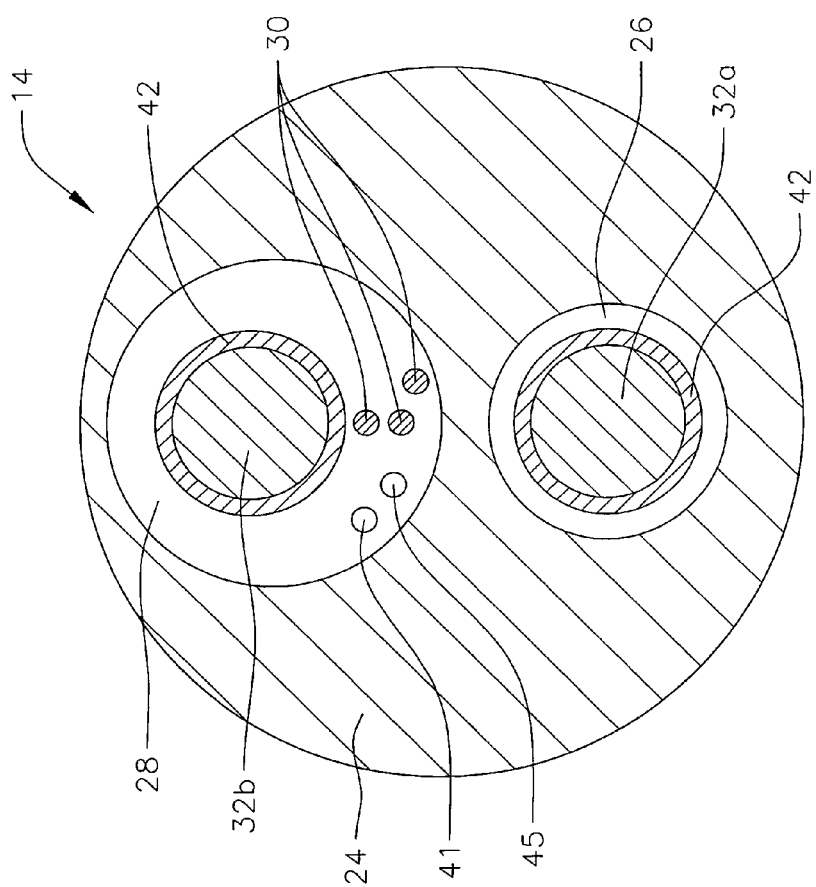
FIG. 3B is a longitudinal cross-sectional view of the tip section of FIG. 3A taken along line 3B-3B.

As shown in FIGS. 2, 3A and 3B, the catheter body 12 comprises an elongated tubular construction having a single axial or central lumen 18. The catheter body 12 is flexible, i.e. bendable, but substantially non-compressible along its length. The catheter body 12 can be of any suitable construction and made of any suitable material. For example, the catheter 10 may comprise an outer wall 20 made of polyurethane or PEBAX. The outer wall 20 can comprise an embedded braided mesh of stainless steel or the like to increase torsional stiffness of the catheter body 12 so that when the control handle 16 is rotated the tip section 14 will rotate in a corresponding manner.

The overall length and diameter of the catheter 10 may vary as desired. In one embodiment, the catheter 10 has an overall length of about 48 inches. The outer diameter of the catheter body 12 is not critical, but in one embodiment is no more than about 8 french. The inner surface of the outer wall 20 can be lined with a stiffening tube 22, which can be made of any suitable material, such as nylon or polyimide. The stiffening tube 22, along with the braided outer wall 20, provides improved flexural and torsional stability while at the same time minimizing the wall thickness of the catheter body 12, thus maximizing the diameter of the central lumen 18. The outer diameter of the stiffening tube 22 is about the same as or slightly smaller than the inner diameter of the outer wall 20. In one embodiment, the catheter 10 has an outer diameter of about 0.092 inch and a lumen 18 diameter of about 0.052 inch. If desired, the stiffening tube 22 can be omitted.

One means for attaching the catheter body 12 to the tip section 14 is illustrated in FIGS. 2 and 3A. The proximal end of the tip section 14 comprises an outer circumferential notch 34 that receives the inner surface of the outer wall 20 of the catheter body 12. The tip section 14 and catheter body 12 are attached by glue or the like. Before the tip section 14 and the catheter body 12 are attached, however, the stiffening tube 22 is inserted into the catheter body 12. The distal end of the stiffening tube 22 is fixedly attached near the distal end of the catheter body 12 by forming a glue joint with polyurethane glue or the like. A small distance, e.g. about 3 mm, is provided between the distal end of the catheter body 12 and the distal end of the stiffening tube 22 to permit room for the catheter body 12 to receive the notch 34 of the tip section 14. A force is applied to the proximal end of the stiffening tube 22, and while the stiffening tube 22 is under compression, a first glue joint (not shown) is made between the stiffening tube 22 and the outer wall 20 by a fast drying glue, e.g. Super Glue®. Thereafter, a second glue joint is formed between the proximal ends of the stiffening tube 22 and outer wall 20 using a slower drying, but stronger glue, e.g. polyurethane.

A spacer 36 lies within the catheter body 12 between the distal end of the stiffening tube 22 and the proximal end of the tip section 14. The spacer 36 is made of a material that is stiffer than the material of the tip section 14, i.e. polyurethane, but not as stiff as the material of the stiffening tube 22, i.e. polyimide. One suitable material for the spacer 36 is Teflon®. The spacer 36 has outer and inner diameters about the same as the outer and inner diameters of the stiffening tube 22. The spacer 36 provides a transition in flexibility at the junction of the catheter body 12 and the tip section 14 to bend smoothly without folding or kinking. If desired, the spacer 36 can be omitted.

The tip section 14 comprises a short section of flexible tubing 24 having at least two lumens. The flexible tubing 24 is made of a suitable non-toxic material that is preferably more flexible than the catheter body 12. One exemplary material for the tubing 24 is braided polyurethane, i.e. polyurethane with an embedded mesh of braided stainless steel or the like. The outer diameter of the tip section 14, like that of the catheter body 12, is no greater than about 8 french. In another embodiment, the tubing 24 is about 6.5 french or less.

In one embodiment, as shown in FIGS. 2, 3A and 3B, the tubing 24 has a first off-axis lumen 26 for a first puller wire 32a and a second off-axis lumen 28 for a second puller wire 32b. The off-axis lumens 26 and 28 are generally aligned along a diameter of the of the tip section 14. In the depicted embodiment, the off-axis lumens 26 and 28 are asymmetrical and therefore non-interchangeable. The first off-axis lumen 26 is smaller than the second off-axis lumen 28 which carries additional components such as lead wires and thermocouple wires. In an 8 french or 7 french diameter catheter, where the tip section is 6.5 french, the first off-axis lumen 26 has a diameter ranging from about 0.018 inch to about 0.025 inch, preferably from about 0.018 inch to about 0.022 inch. The second off-axis lumen 28 has a diameter ranging from about 0.022 inch to about 0.030 inch, more preferably from about 0.026 inch to about 0.028 inch.

The first and second puller wires 32a and 32b extend through the catheter 10. Each puller wire 32a and 32b extends from the control handle 16, through the central lumen 18 of the catheter body 12 and into one of the off-axis lumens 26 and 28 of the tip section 14 for deflection of the tip section 14 in a first direction toward the first lumen 26 and a second direction generally opposite to the first direction toward the second lumen 28. As described in more detail below, the proximal end of each puller wire 32a and 32b is anchored within the control handle 16 and the distal end of each puller wire 32 may be anchored at different (unequal) distal distances from the control handle for different bi-directional deflection characteristics in the tip section 14.

Each puller wire 32a and 32b is made of any suitable metal, such as stainless steel or Nitinol. In one embodiment, each puller wire 32a and 32b has a coating, such as Teflon® or the like. Each puller wire 32a and 32b has a diameter ranging from about 0.006 inch to about 0.0010 inch. The puller wires 32a and 32b can have the same diameter.

In the illustrated embodiment of FIGS. 2, 3A and 3B, the distal end of each puller wire 32a and 32b is anchored near the distal end of the tip section 14, for example, in blind holes 37 in the tip electrode 38 by welding or the like. Accordingly, for this embodiment, the bi-directional deflection of the tip section in the first and second directions is generally symmetrical.

Figure 6A:
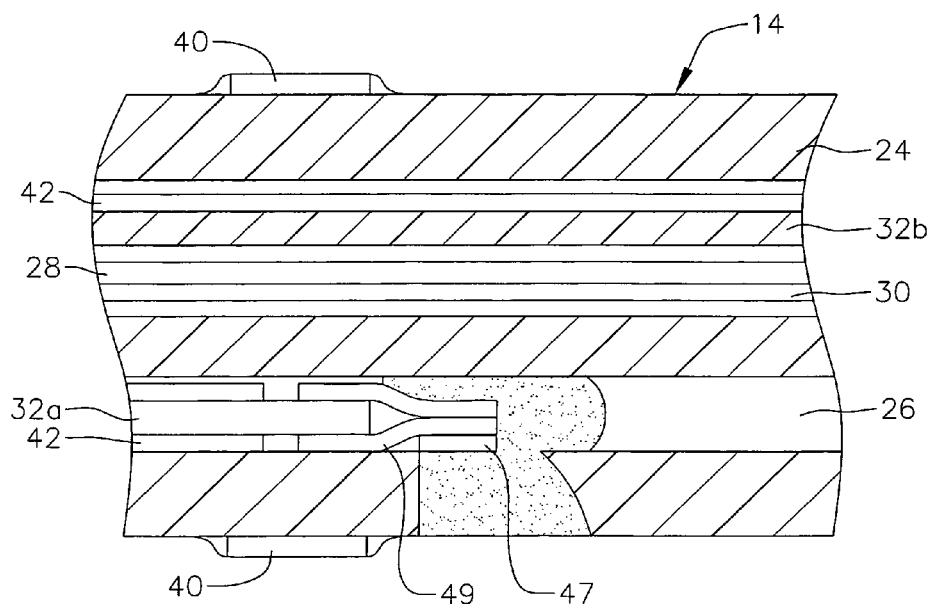
FIG. 6a is a transverse cross-sectional view of a catheter tip section according to one embodiment of the present invention where the puller wires are anchored to the side walls of the tip section.
Figure 6B:
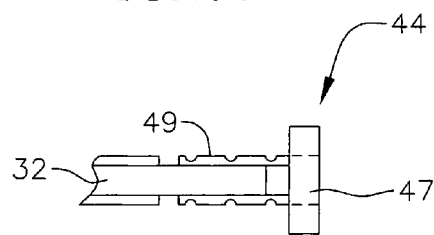
FIG. 6b is a longitudinal cross-sectional view of an exemplary puller wire T-bar anchor.
Figure 7:
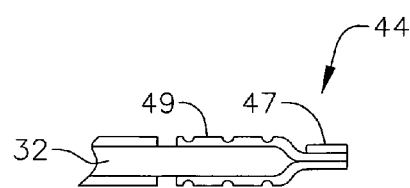
FIG. 7 is a longitudinal cross-sectional view of the T-bar anchor of FIG. 6b rotated 90° to show the cross piece on end.

Alternatively, the distal ends of the puller wires may be anchored at different distal locations for symmetrical or asymmetrical "S" shape deflection. For example, the first puller wire 32a extending through the first off-axis lumen 26 in the tip section can have its distal end anchored to the side wall of the tip section 14 at a location that is proximal of the anchored distal end of the second puller wire 32b in the tip electrode. As shown in FIGS. 6a, 6b and 7, the first puller wire 32a is attached to the side wall by means of an anchor 44 fixedly attached to the distal end of the puller wire 32a. The anchor 44 is formed by a metal tube 49, e.g., a short segment of hypodermic stock, that is fixedly attached, e.g. by crimping, to the distal end of the puller wire 32a. The tube has a section that extends a short distance beyond the distal end of the puller wire 32a. A cross-piece 47 made of a small section of stainless steel ribbon or the like is soldered or welded in a transverse arrangement to the distal end of the metal tube which is flattened during the operation. This creates a T-bar anchor 44. A notch is created in the side of the tip section 14 resulting in an opening in the off-axis lumen 26 carrying the puller wire 32a. The cross piece 47 lies transversely within the notch. Because the length of the ribbon forming the cross-piece 47 is longer than the diameter of the opening into the off-axis lumen 26, the anchor 44 cannot be pulled completely into the off-axis lumen 26. The notch is then sealed with polyurethane glue or the like to give a smooth outer surface. The glue flows into the off-axis lumen 26 to fully secure the anchor. A tunnel (not shown), in the form of polyimide tubing or the like, can be provided to permit passage of the lead wire 30 through the glue. This same puller wire anchor construction can be used to anchor the second puller wire 32b in the second off-axis lumen 28. Other means for anchoring the puller wires 32a and 32b in the tip section 14 would be recognized by those skilled in the art and are included within the scope of this invention.

Figure 4A:
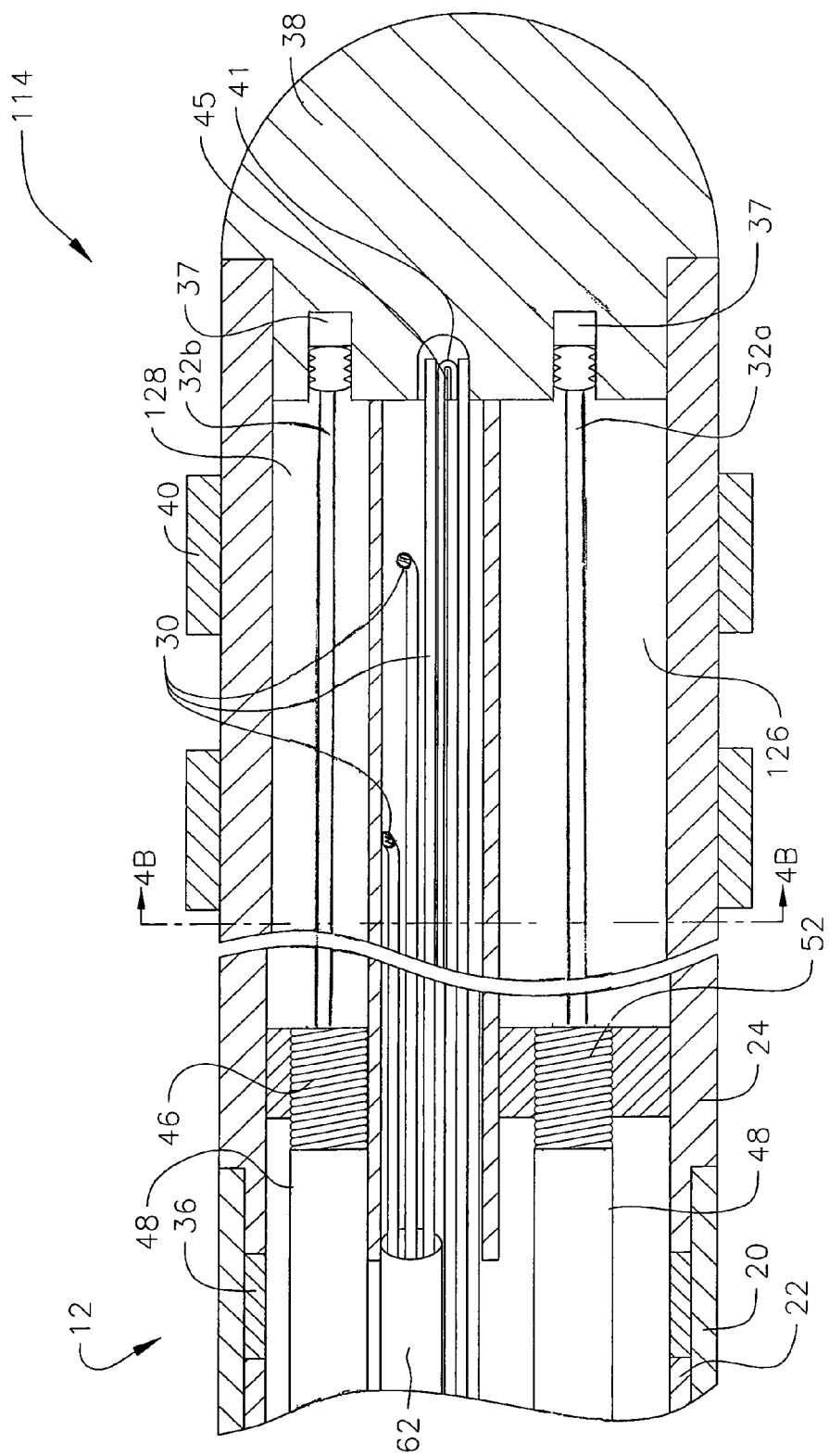
FIG. 4A is a side cross-sectional view of a tip section according to another embodiment of the present invention, including the junction between the catheter body and tip section.

Although the tubing 24 of the tip section is illustrated and described above as having two asymmetrical lumens, it is understood that the number and size of the lumens in the tip section may vary as desired. For example, in another alternative embodiment, as shown in FIGS. 4A and 4B, the tubing 124 of the tip section 114 has three lumens 126, 127 and 128. In this embodiment, the first lumen 126 carries the first puller wire 32a, the third lumen 128 carries the second puller wire 32b, and the second lumen 127 carries any remaining wires, cables and tubes, such as lead wires, thermocouple wires and/or an electromagnetic sensor cable. In this embodiment, the lumens 126, 127 and 128 may be equal in size, or the second lumen 127 may be slightly larger than the other lumens 126 and 128.

Figure 5A:
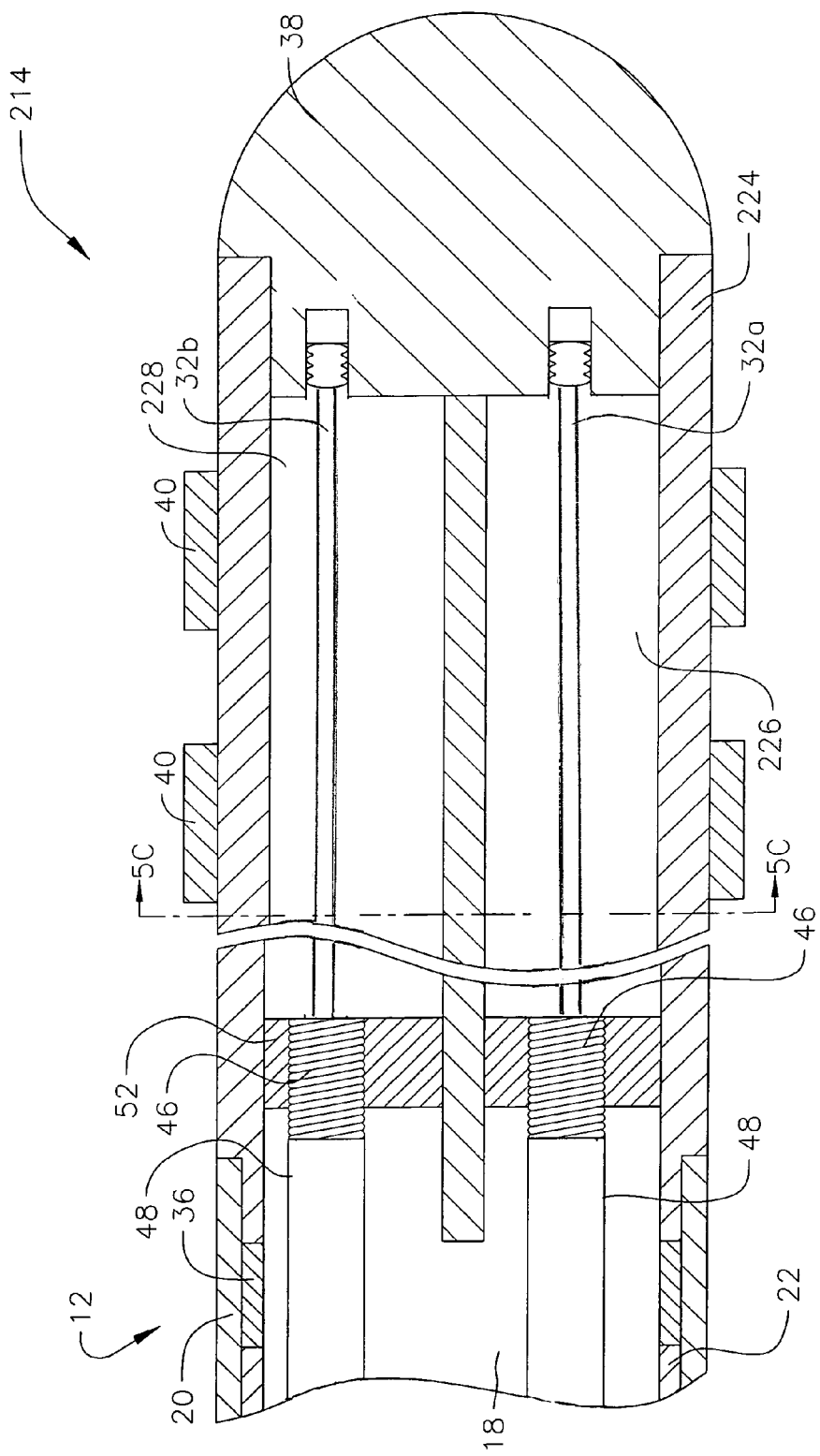
FIG. 5A is a side cross-sectional view of a tip section according to yet another embodiment of the present invention, including the junction between the catheter body and tip section.
Figure 5B:
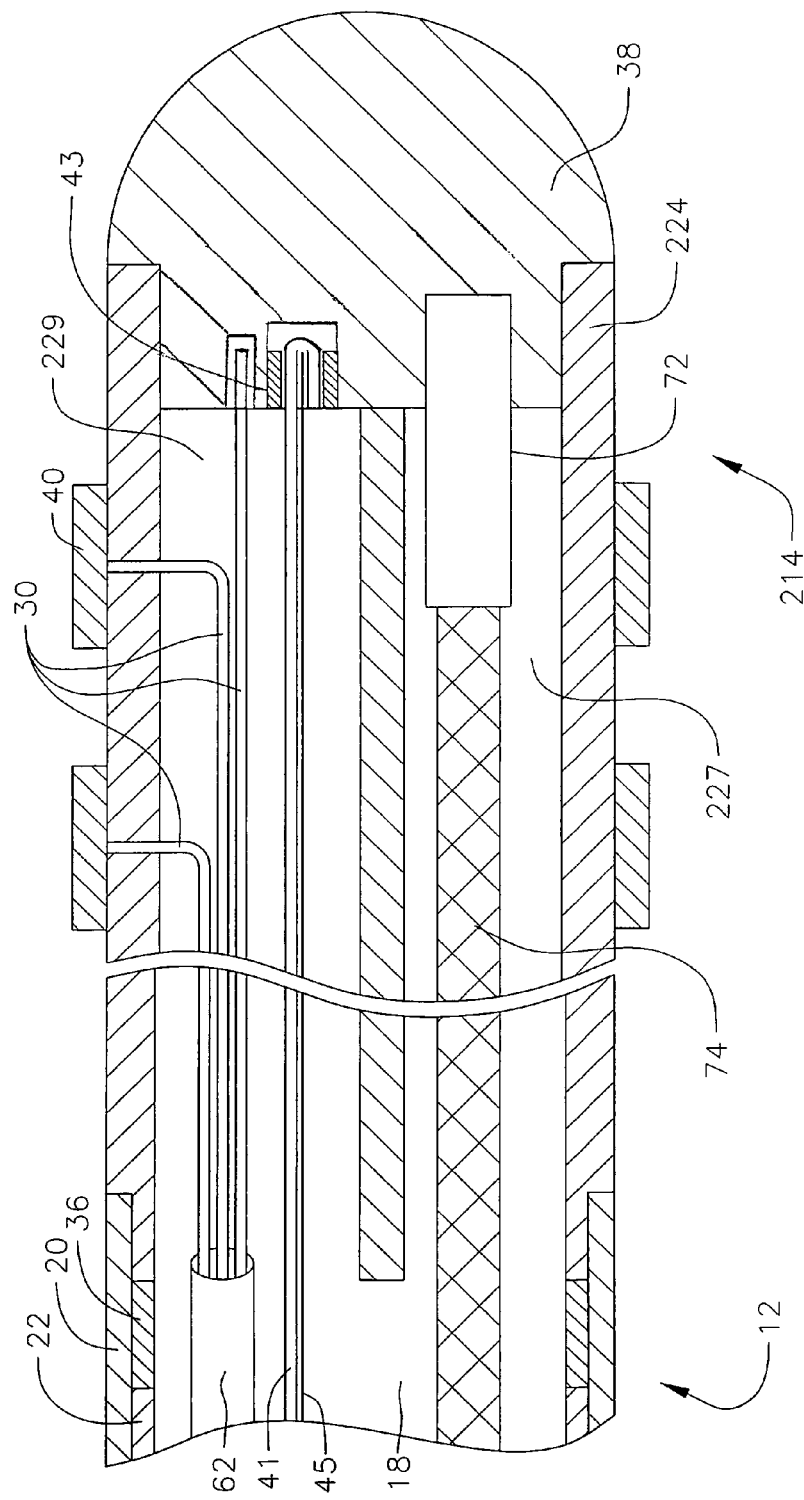
FIG. 5B is a side cross-sectional view of the tip section of FIG. 5A taken of the side opposite that of FIG. 5A.
Figure 5C:
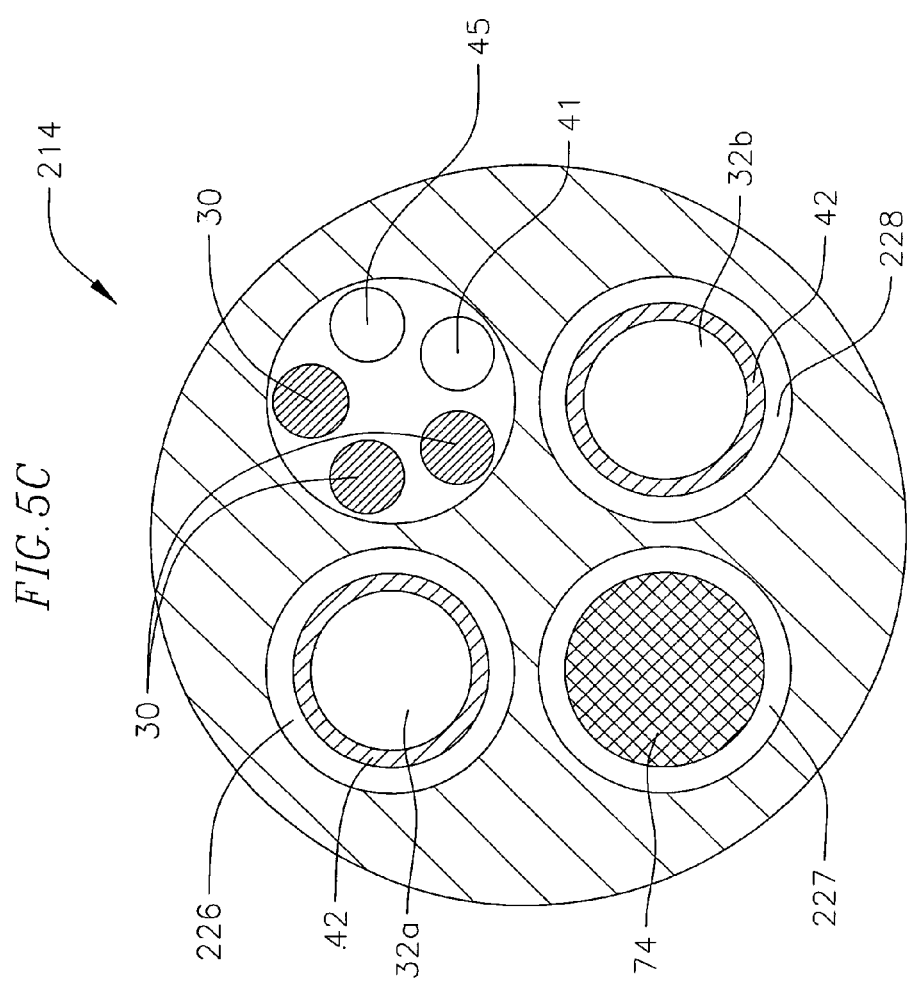
FIG. 5C is a longitudinal cross-sectional view of the tip section of FIG. 5A taken along line 5C-5C.

Alternatively, as shown in FIGS. 5A, 5B and 5C, the tubing 224 may have four lumens 226, 227, 228 and 229. In this embodiment, the first lumen 226 carries the first puller wire 32a, the third lumen 228 (generally opposite of the first lumen) carries the second puller wire 32b, the second lumen 227 carries an electromagnetic sensor cable, and the fourth lumen 229 carries any remaining wires, cables and tubes, such as electrode lead wires and/or thermocouple wires. In this embodiment, the lumens 226, 227, 228 and 229 may be equal in size, or the second and fourth lumens 227 and 229 may be slightly larger than the other lumens 226 and 228.

As shown in FIGS. 3A, 4A and 5A, the distal end of the tip section carries a tip electrode 38. Mounted along the length of the tip section is at least one ring electrode 40. The length of the ring electrode 40 is not critical, but can range from about 1 mm to about 3 mm. Additional ring electrodes can be provided if desired. If multiple ring electrodes are used, they can be spaced apart in any desired fashion so long as their edges do not touch.

The tip electrode 38 and ring electrodes 40 are each connected to a separate lead wire 30. In the two lumen tip section 14 embodiment of FIG. 3B, each lead wire 30 extends through the second off-axis lumen 28 in the tip section 14, through the central lumen 18 in the catheter body 12 and through the control handle 16. In the three lumen embodiment of the tip section 14 of FIG. 4B, the lead wires 30 extend through the second lumen 127 of the tubing 24. In the four lumen embodiment of the tip section 14 of FIG. 5C, the lead wires 30 extend through the fourth lumen 229 of the tubing 24. The proximal end of each lead wire 30 extends out the proximal end of the control handle 16 and is connected to an appropriate connector (not shown), which can be plugged into or otherwise connected to a suitable monitor, source of energy, etc.

The lead wires 30 are connected to the tip electrode 38 and ring electrode 40 by any conventional technique. For example, connection of a lead wire 30 to the tip electrode is accomplished by solder or the like. Connection of a lead wire 30 to a ring electrode is accomplished by first making a small hole through the tubing 24. Such a hole can be created, for example, by inserting a needle through the tubing 24 and heating the needle sufficiently to form a permanent hole. A lead wire 30 is then drawn through the hole with a microhook or the like. The end of the lead wire 30 is then stripped of any coating and welded to the underside of the ring electrode 40, which is then slid into position over the hole and fixed in place with polyurethane glue or the like.

As shown in FIGS. 2, 4A and 5B, the lead wires 30 are enclosed within a protective sheath 62 to prevent contact with other components within the lumen 18 of the catheter body 12. The protective sheath 62 can be made of any suitable material, preferably polyimide. The protective sheath 62 is anchored at its distal end to the proximal end of the catheter body 12 by gluing it to the side wall of the catheter body 12 with polyurethane glue or the like. As would be recognized by one of ordinary skill in the art, the protective sheath 62 can be eliminated if desired.

The catheter 10 further comprises two compression coils 46, each in surrounding relation to a corresponding puller wire 32a or 32b. Each compression coil 46 is made of any suitable metal, such as stainless steel. Each compression coil 46 is tightly wound on itself to provide flexibility, i.e. bending, but to resist compression. The inner diameter of each compression coil 46 is slightly larger than the diameter of its associated puller wire. For example, when the puller wire has a diameter of about 0.007 inch, the corresponding compression coil has an inner diameter of about 0.008 inch. The coating on the puller wires 32a and 32b allows them to slide freely within the compression coils 46. The outer surface of each compression coil 46 is covered along most of its length by a flexible, non-conductive sheath 48 to prevent contact between the compression coil 46 and the lead wires 30 within the central lumen 18 of the catheter body 12. One example of a suitable material for the non-conductive sheath 48 is thin-walled polyimide tubing.

At the distal end of the catheter body 12, the two compression coils 46 are positioned in diametric opposition and aligned with the two off-axis lumens 26 and 28 in the tip section 14. In the three and four lumen embodiments of the tip section, the compression coils are positioned in the catheter body such that they are aligned with the two lumens housing the puller wires. The compression coils 46 and stiffening tube 22 are sized so that the compression coils fit closely and slidably within the stiffening tube 22. With this design, the lead wires 30 can distribute themselves around the two compression coils 46 without misaligning the coils.

The compression coils 46 are secured within the catheter body 12 with polyurethane glue or the like. Each compression coil 46 is anchored at its proximal end to the proximal end of the stiffening tube 22 in the catheter body 12 by proximal glue joint 50. When a stiffening tube 22 is not used, each compression coil 46 is anchored directly to the outer wall 20 of the catheter body 12.

The distal end of each compression coil 46 is anchored to the proximal end of its corresponding off-axis lumen 26 or 28 by distal glue joint 52. Alternatively, the distal ends of the compression coils 46 may be anchored to the distal end of the stiffening tube 22 in the catheter body 12 or directly to the distal end of the outer wall 20 of the catheter body 12 when no stiffening tube 22 is used. In the depicted embodiment, where the compression coils 46 are each surrounded by a sheath 48, care should be taken to ensure that the sheath is reliably glued to the compression coil. The lead wires 30 can also be anchored in the glue joint. However, if desired, tunnels in the form of plastic tubing or the like can be provided around the lead wires at the glue joint to permit the lead wires to be slidable within the glue joint.

Both glue joints comprise polyurethane glue or the like. The glue may be applied by means of a syringe or the like through a hole made between the outer surface of the catheter body 20 and the central lumen 18. Such a hole may be formed, for example, by a needle or the like that punctures the outer wall 18 and stiffening tube 22 and is heated sufficiently to form a permanent hole. The glue is then introduced through the hole to the outer surface of the compression coil 46 and wicks around the outer circumference to form a glue joint about the entire circumference of each sheath 48 surrounding each compression coil 46. Care should be taken to ensure that glue does not wick over the end of the coil, preventing the puller wire from sliding within the coil.

Within the lumens of the tip section 14, each puller wire 32a and 32b is surrounded by a plastic sheath 42, which can be made of Teflon® (see FIGS. 3B, 4B and 5C). The plastic sheathes 42 prevent the puller wires 32a and 32b from cutting into the wall of the tip section when the tip section is deflected. Each sheath 42 ends near the distal end of each puller wire 32a and 32b. Alternatively, each puller wire 32a and 32b can be surrounded by a compression coil where the turns are expanded longitudinally, relative to the compression coils extending through the catheter body, such that the surrounding compression coil is both bendable and compressible.

The catheter may further comprise one or more temperature sensing means for sensing the temperature of the tip electrode and/or ring electrodes. Any conventional temperature sensing means, e.g. a thermocouple or thermistor, may be used. In one embodiment, as shown in FIGS. 3A, 4A and 5B, the temperature sensing means comprises a thermocouple formed by an enameled wire pair. One wire of the wire pair is a copper wire 41, e.g. a number 40 copper wire. The other wire of the wire pair is a constantan wire 45, which supports and strengthens the wire pair. The wires 41 and 45 of the wire pair are electrically isolated from each other except at their distal ends where they are twisted together, covered with a short piece of plastic tubing 43, e.g. polyimide tubing, and covered with epoxy. When used to sense the temperature of the tip electrode, the plastic tubing 43 is attached in a blind hole in the tip electrode by polyurethane glue or the like. When used to sense the temperature of a ring electrode, the plastic tubing 43 is attached to the underside of the ring electrode by polyurethane glue or the like. In the two lumen tip section embodiment of FIG. 3A, the wires 41 and 45 extend through the first lumen 26 of the tip section 14, through the central lumen 18 of the catheter body 12 and into the control handle 16. In the three lumen tip section embodiment of FIG. 4A, the wires 41 and 45 extend through the second lumen 127 of the tip section 114, through the central lumen 18 of the catheter body 12 and into the control handle 16. In the four lumen tip section embodiment of FIG. 5B, the wires 41 and 45 extend through the fourth lumen 229 of the tip section 214, through the central lumen 18 of the catheter body 12 and into the control handle 16. The wires 41 and 45 extend through the control handle 16 to a connector (not shown) connectable to a temperature monitor.

The catheter may also further comprise an electromagnetic sensor 72 mounted within another blind hole in the tip electrode. The electromagnetic sensor is 72 is connected to an electromagnetic sensor cable 74, which extends through a lumen in the tip section. In the four lumen embodiment of the tip section of FIG. 5B, the cable 74 extends through the second lumen 227 of the tip section. It is understood by one of ordinary skill in the art that in the two lumen embodiment of the tip section of FIG. 3A the electromagnetic sensor cable 74 can extend through the first lumen 26 of the tip section and that in the three lumen embodiment of the tip section of FIG. 4A, the cable 74 can extend through the second lumen 127 of the tip section. From the tip section, the cable 74 extends through the central lumen 18 of the catheter body and out through the control handle. The cable 74 then extends out the proximal end of the control handle 16 within an umbilical cord (not shown) to a sensor control module (not shown) that houses a circuit board (not shown). The electromagnetic sensor cable 74 comprises multiple wires encased within a plastic covered sheath. In the sensor control module, the wires of the cable 74 are connected to the circuit board. The circuit board amplifies the signal received from the electromagnetic sensor 72 and transmits it to a computer in a form understandable by the computer. Because the catheter is designed for a single use only, the circuit board may contain an EPROM chip which shuts down the circuit board approximately 24 hours after the catheter has been used. This prevents the catheter, or at least the electromagnetic sensor, from being used twice.

Suitable electromagnetic sensors for use with the present invention are described, for example, in U.S. Pat. Nos. 5,558,091, 5,443,489, 5,480,422, 5,546,951, 5,568,809 and 5,391,199 and International Publication No. WO 95/02995, the entire disclosures of which are incorporated herein by reference. One exemplary sensor 72 has a length of from about 6 mm to 7 mm and a diameter of about 1.3 mm.

Figure 8:
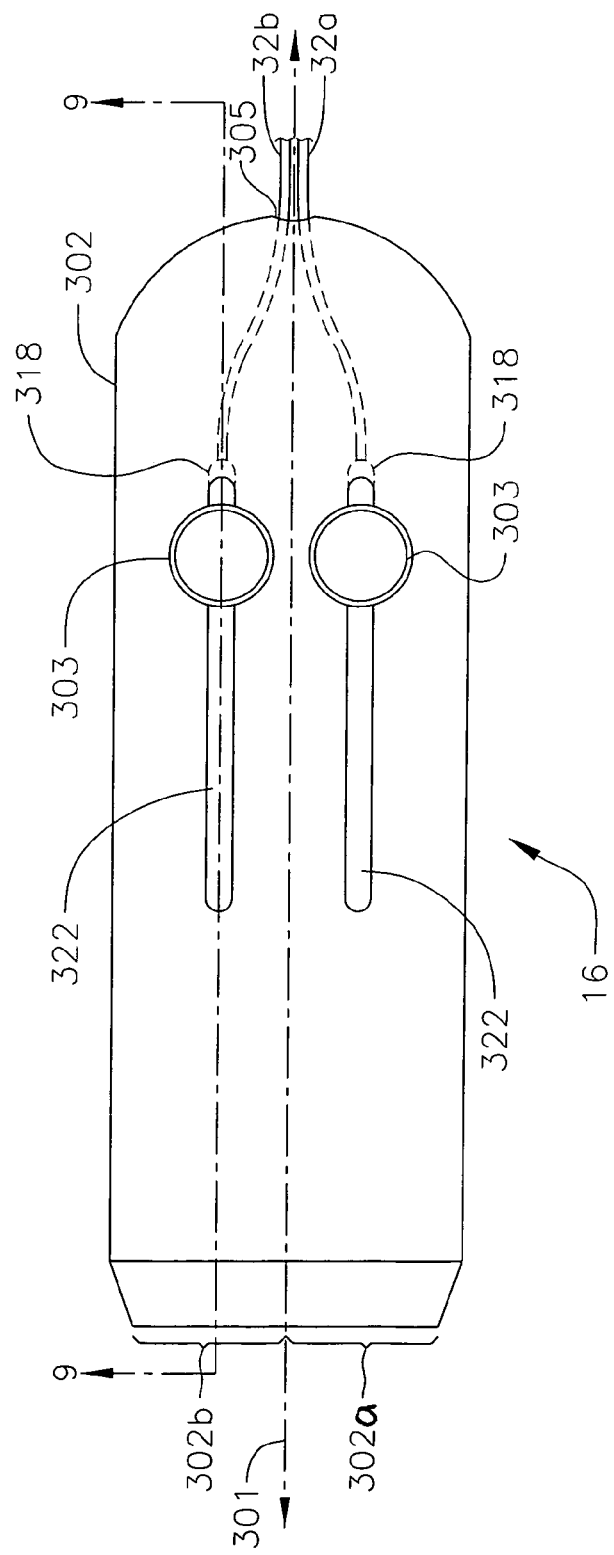
FIG. 8 is a top view of a handle according to one embodiment of the present invention.
Figure 9:
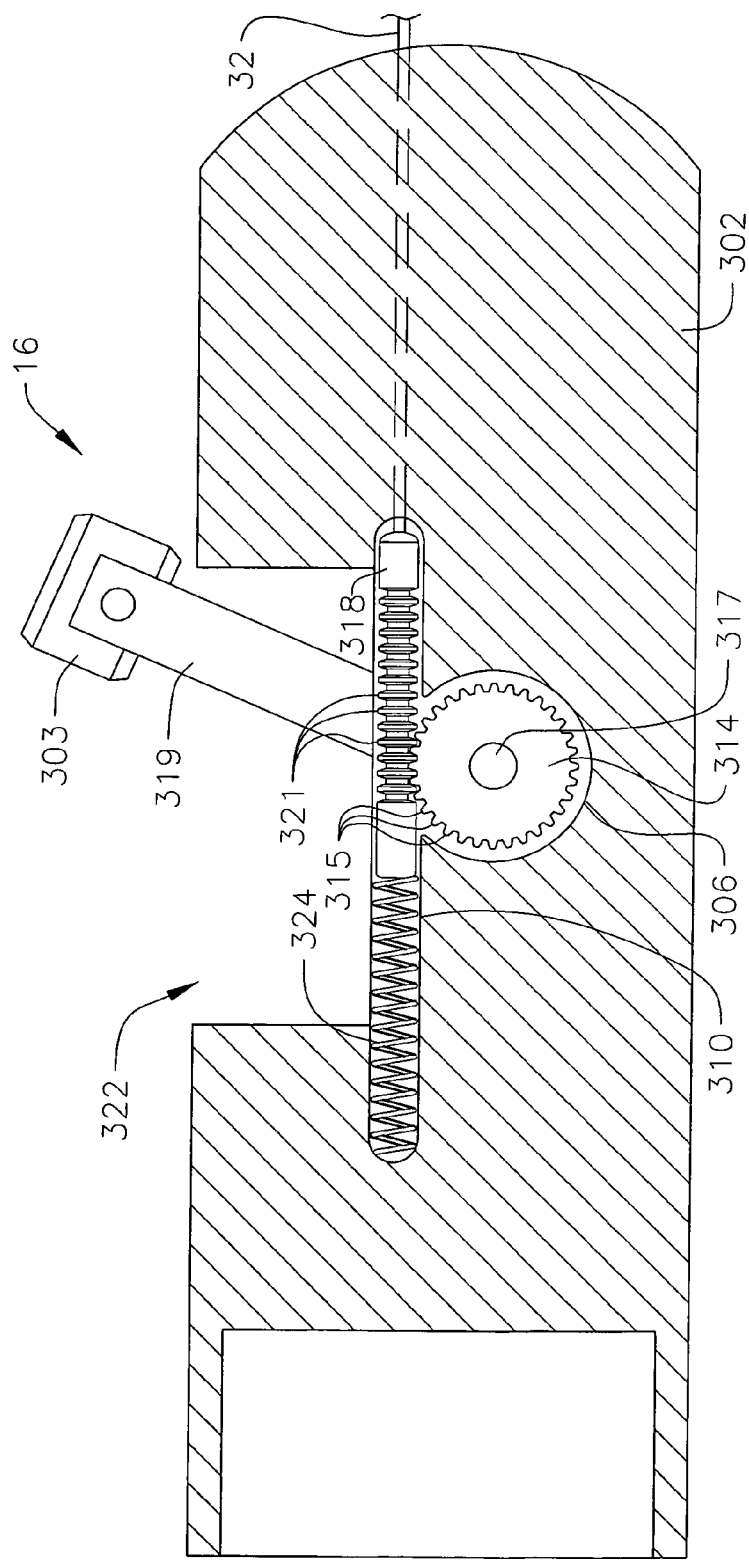
FIG. 9 is a side cross-sectional view of the handle of FIG. 8 taken along line 9-9, with a lever in a neutral distal position.

Longitudinal movement of puller wire 32a and/or puller wire 32b relative to the catheter body 12, which results in deflection of the tip section 14, is accomplished by suitable manipulation of the control handle 16. As shown in FIGS. 8 and 9, one suitable control handle 16 comprises a generally hollow, generally tubular handle housing 302 having a longitudinal axis and proximal and distal ends. The catheter body 12 is fixedly attached in a passage 305 at the distal end of the housing 302 by means of a glue joint and shrink sleeve as is known in the art. The puller wires 32a and 32b, lead wires 30 and any other wires, cables or tubes that extend through the catheter body extend through the passage 305 in the housing 302. The puller wires 32a and 32b proximal the passage 305 diverge slightly from each other toward their respective deflection means and mechanism for dual and, where desirable, substantially independent manipulation of each puller wire.

In the illustrated embodiment, the handle housing 302 is generally symmetrical about its longitudinal dimension 301 such that a right half 302a and a left half 302b generally mirror each other. In that regard, the following description is directed to the left half 302b with the understanding by one of ordinary skill in the art that the description applies to the right half 302a.

Figure 10A:
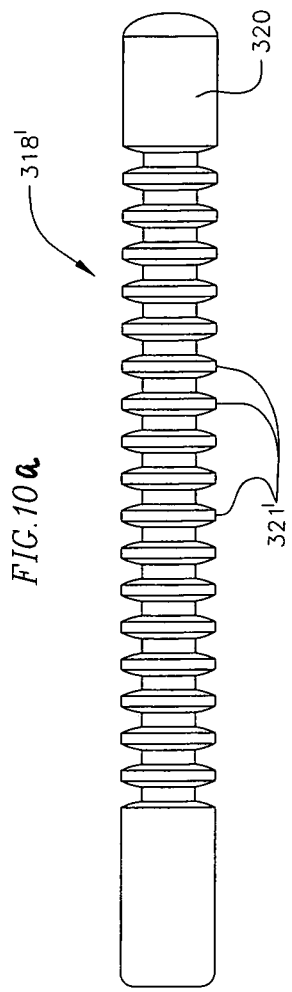
FIG. 10a is a side view of a carrier according to one embodiment of the present invention.
Figure 10C:
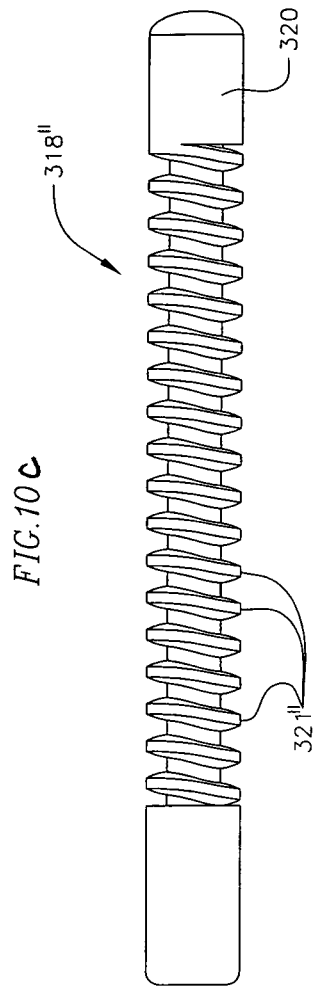
FIG. 10c is a side view of a carrier according to another embodiment of the present invention.
Figure 10B:
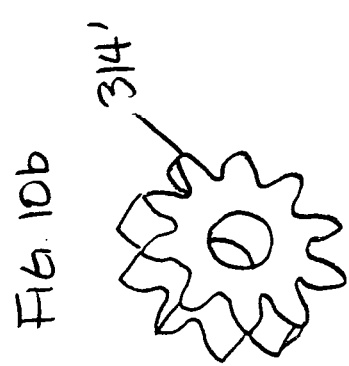
Figure 10D:
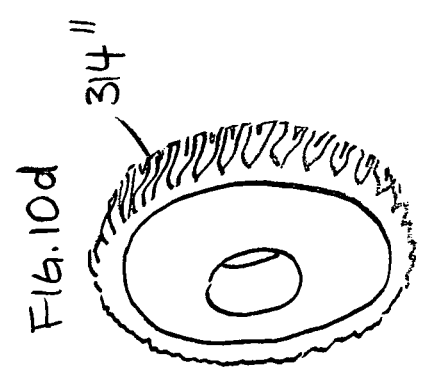
FIG. 10d is a perspective view of a gear according to another embodiment of the present invention, suitable for use with the carrier of FIG. 10c.

In the housing half 302, the deflection means and mechanism comprise means for converting rotational or pivotal movement into linear or longitudinal movement. In the illustrated embodiment, such means comprise a spur gear 314 in engagement with an elongated carrier 318 to which the proximal end of the puller wire 32 is anchored. The spur gear 314 is rotationally coupled to a lever 319 by a pin 317. The lever 319 extends through a longitudinal slot 322 whose distal and proximal ends limit the distal and proximal positions of the lever. Accordingly, as an operator of the catheter 10 pivots the lever 319 by its thumb control 303 about the pin 317, the gear 314 rotates counterclockwise or clockwise, which in turn moves the carrier 318 distally or proximally, respectively. The gear 314 may be, for example, a pinion 314' (FIG. 10b), or a wormwheel 314" (FIG. 10d). The carrier 318 may be, for example, a rack 318' with teeth 321' (FIG. 10a) that engages linear teeth 315 of the pinion, or a worm 318" with a spiral groove 321" (FIG. 10b) that engages angled teeth 315 of the wormwheel. In any case, the gear 314 and the carrier 318 engage each other such that upon rotation of the gear 314, the carrier 318 translates distally or proximally to advance or draw, respectively, the puller wire anchored thereto. It is understood by one of ordinary skill in the art that depending on the desired ratio of rotation to translation between the gear and the carrier, one can vary various parameters and dimensions, including the diameter of the gear 314, the length of the toothed portion of the carrier 318, and the size/plurality of the teeth of the gear and the carrier.

The handle housing 302 is configured with a generally circular cavity 306 to house the gear 314 and a generally elongated channel 310 to house the carrier 318. Opposing ends of the pin 317 rotationally coupling the gear 314 and the lever 319 are supported in the housing 302 such that the rotational axis of the gear 314 is fixed relative to the housing 302 but the gear is suspended in the cavity 306 and free to rotate about the axis in order to drive the carrier 318 distally or proximally. The channel 310 is configured and sized to guide the carrier 318 to move in a longitudinal direction and prevent the carrier 318 from disengaging the gear 314. The length of the channel 310 accommodates the distal and/or proximal movement of the carrier 318 as caused by the movement of the lever 319 by an operator of the catheter.

The carrier 318 can be biased toward a "resting" position within the channel 310 by a bias member 324. In the illustrated embodiments, the bias member is a spring whose distal end is fixedly attached to the proximal end of the carrier 318 and whose proximal end is fixedly attached to the proximal end of the channel 310. However, it is understood that the bias member may include a spring positioned proximally the carrier in the channel 310 as an alternative or in addition to the spring positioned distally the carrier.

Figure 9A:
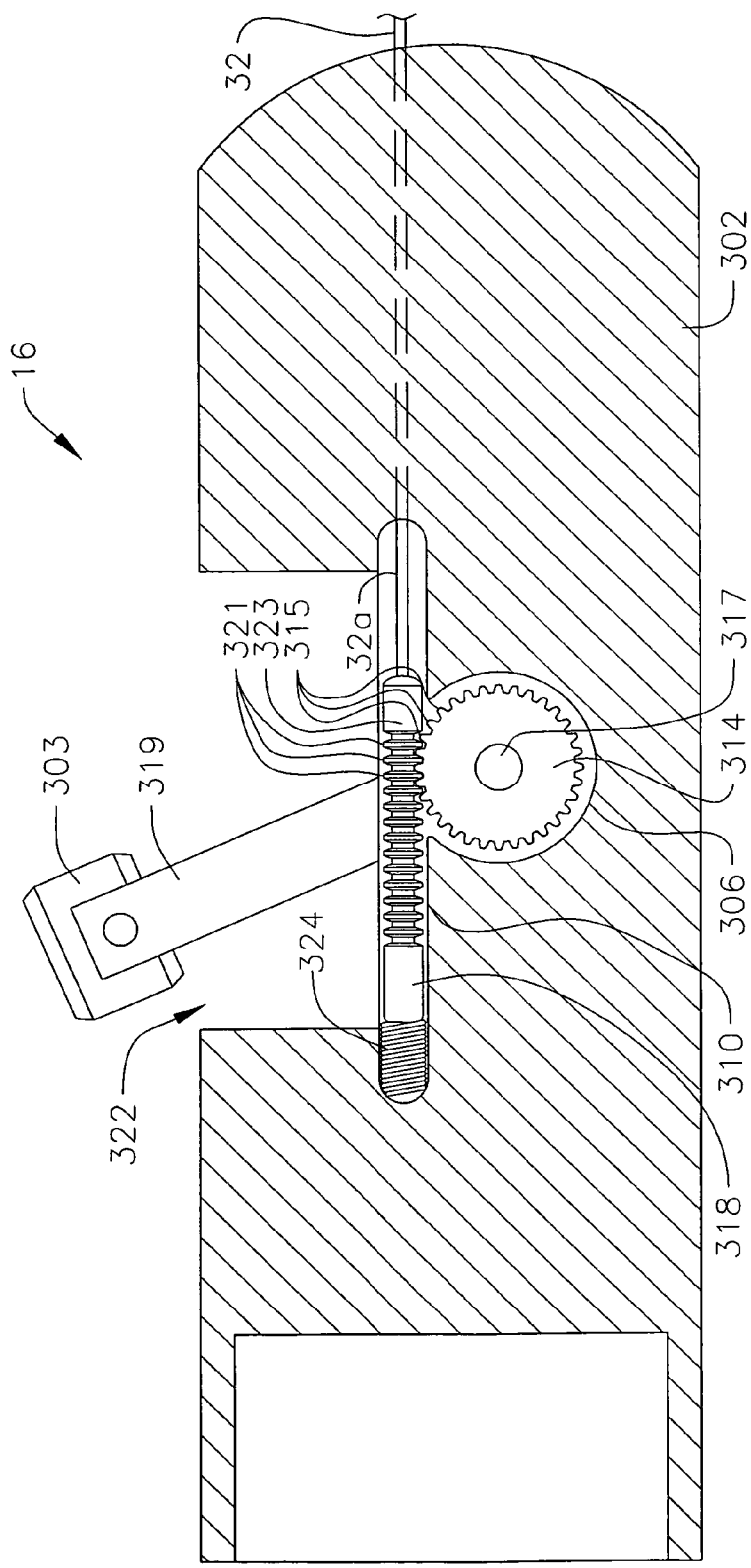
FIG. 9A is a side cross-sectional view of the handle of FIG. 9 depicted with the lever in an actuated proximal position.

The embodiment of the deflection means depicted in FIG. 9 shows the lever 319 having its most distal position as its resting or neutral position, with no intended catheter deflection. The gear 314 is engaged with the carrier 318 at or near its proximal end which positions the anchored distal end of the puller wire at a greater or maximum length distally from the distal end of the control handle. As biased by the bias member 324 toward its most distal position, the lever 319 assumes or returns to this position when not subjected to a force in the proximal direction. But, when subjected to such a force in the proximal direction sufficient to overcome the bias member, as applied by, e.g., the thumb of the catheter operator, the deflection means in the control handle are as shown in FIG. 9A. In particular, the spring 324 is compressed and the gear 314 is engaged with the carrier 318 at or near its distal end which draws the distal end of the puller wire closer or as close as possible to the distal end of the control handle and results in catheter deflection in the direction of the off-axis puller wire drawn proximally.

Figure 11:
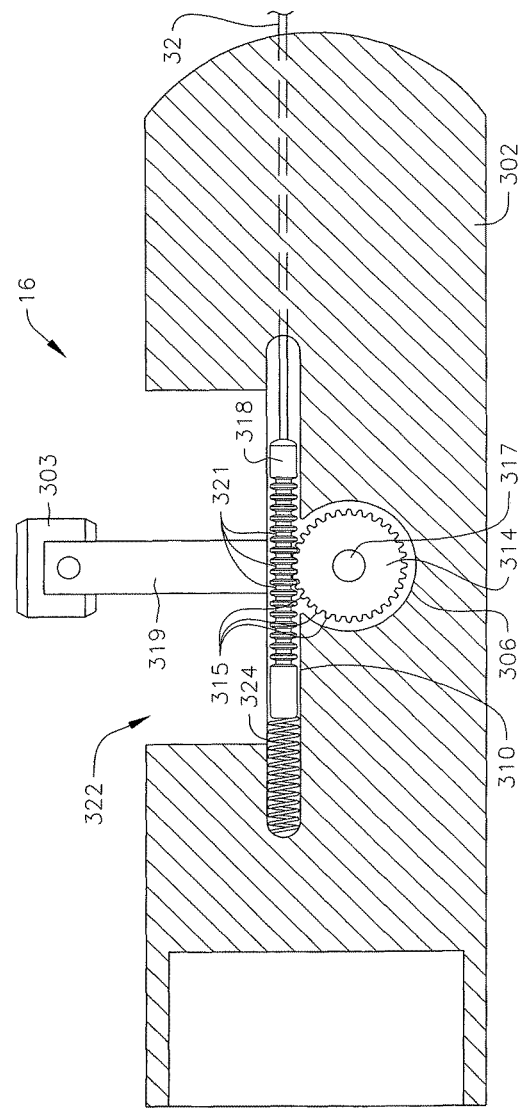
FIG. 11 is a side cross-sectional view of the handle according to another embodiment of the present invention, with a lever in a neutral central position.
Figure 11A:
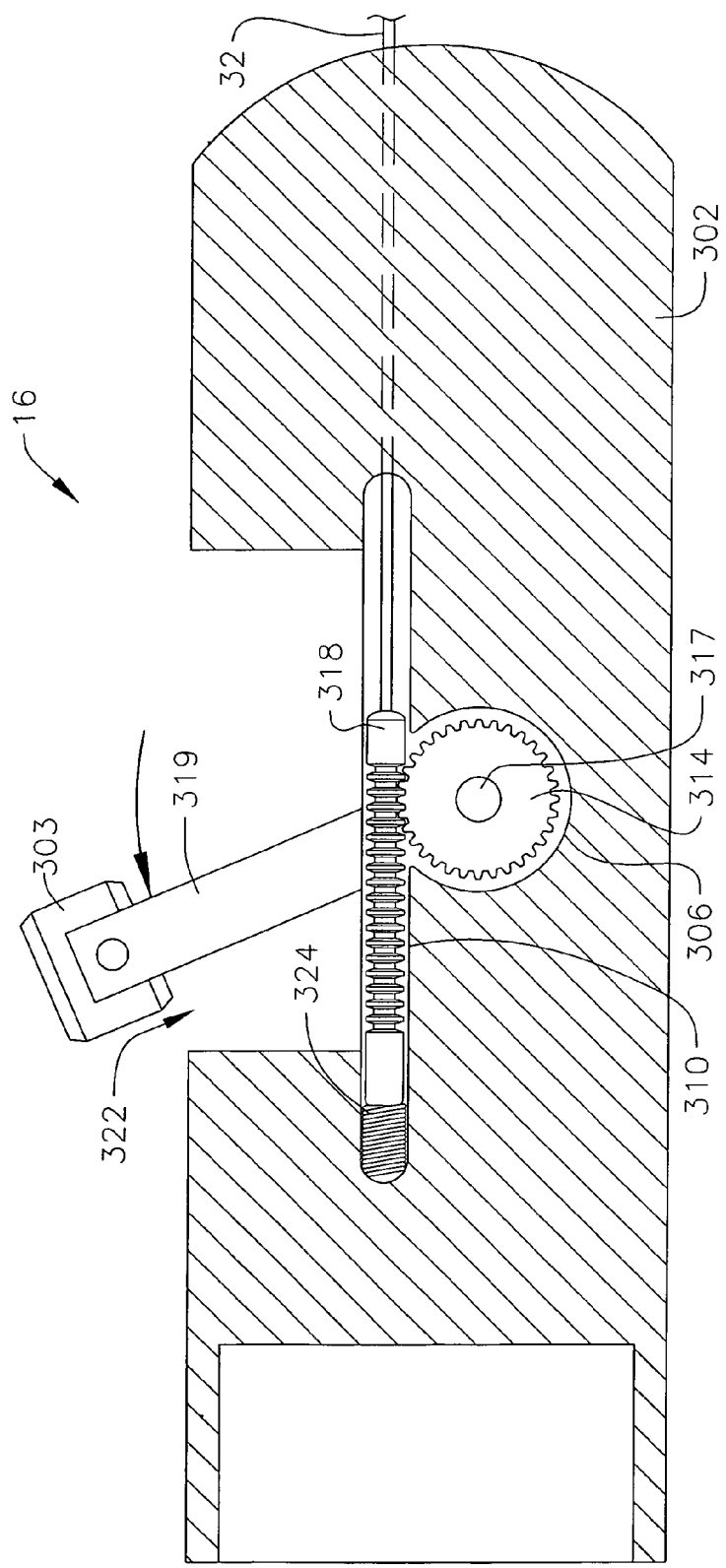
FIG. 11A is a side cross-sectional view of the handle of FIG. 11 depicted with the lever in an actuated proximal position.

Alternatively, another embodiment of the deflection means depicted in FIG. 11. shows the lever 319 having its central position as its resting or neutral position, with no intended catheter deflection. The gear 314 is engaged with the carrier 318 (which may have a longer toothed portion) at or near its longitudinal center which positions the distal end of the puller wire at mid-distance distally from the distal end of the control handle. As biased by the bias member 324 toward its central position, the lever 319 assumes or returns to this position when not subjected to a force in the proximal or distal direction. But, when subjected to such a force in the proximal direction sufficient to overcome the bias member, as applied by, e.g., the thumb of the catheter operator, the deflection means in the control handle are as shown in FIG. 11A. In particular, the spring 324 is compressed and the gear 314 is engaged with the carrier 318 at or near its distal end which draws the distal end of the puller wire closer or as close as permitted to the distal end of the control handle and results in catheter deflection in the direction of the off-axis puller wire drawn proximally.

Figure 11B:
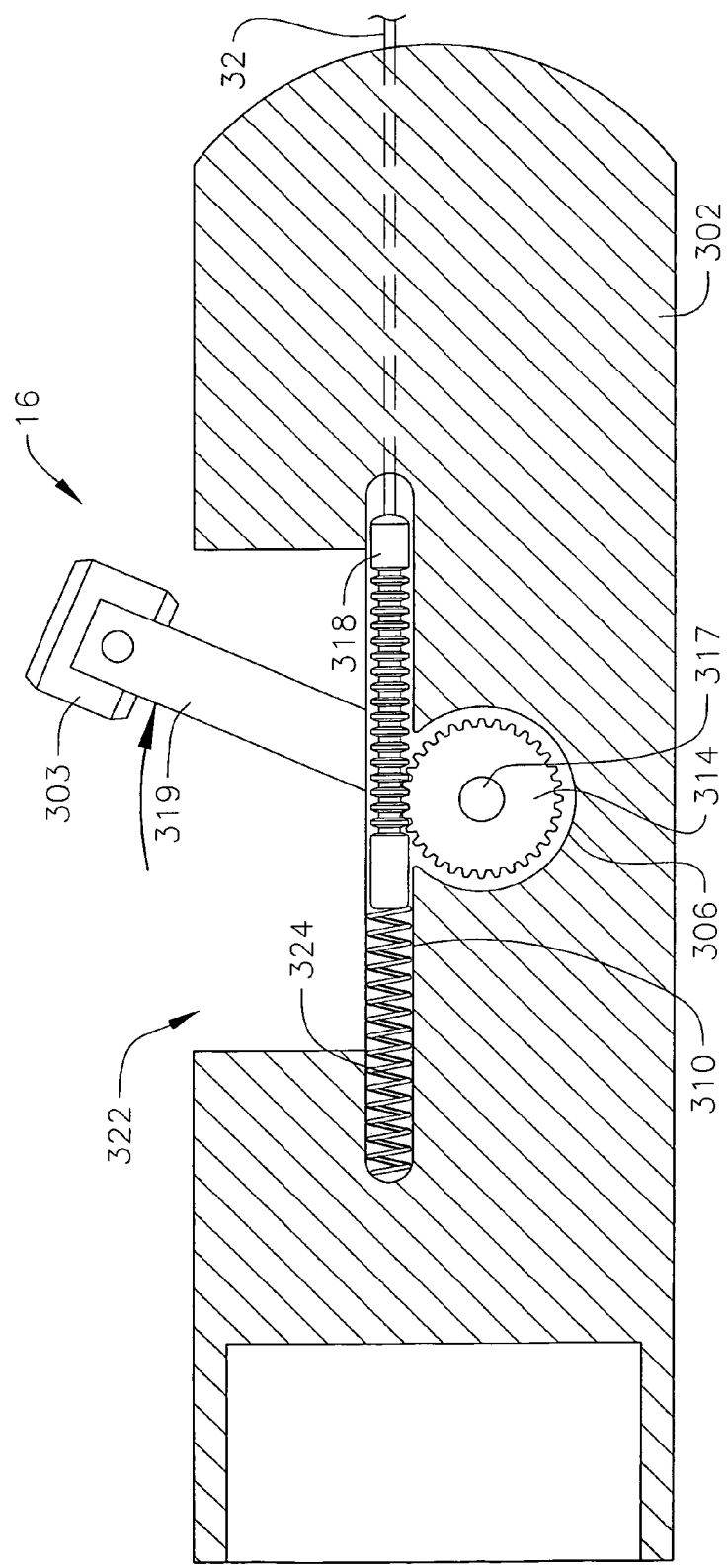
FIG. 11B is a side cross-sectional view of the handle of FIG. 11 depicted with the lever in an effected distal position.
Figures 12A, 12B:
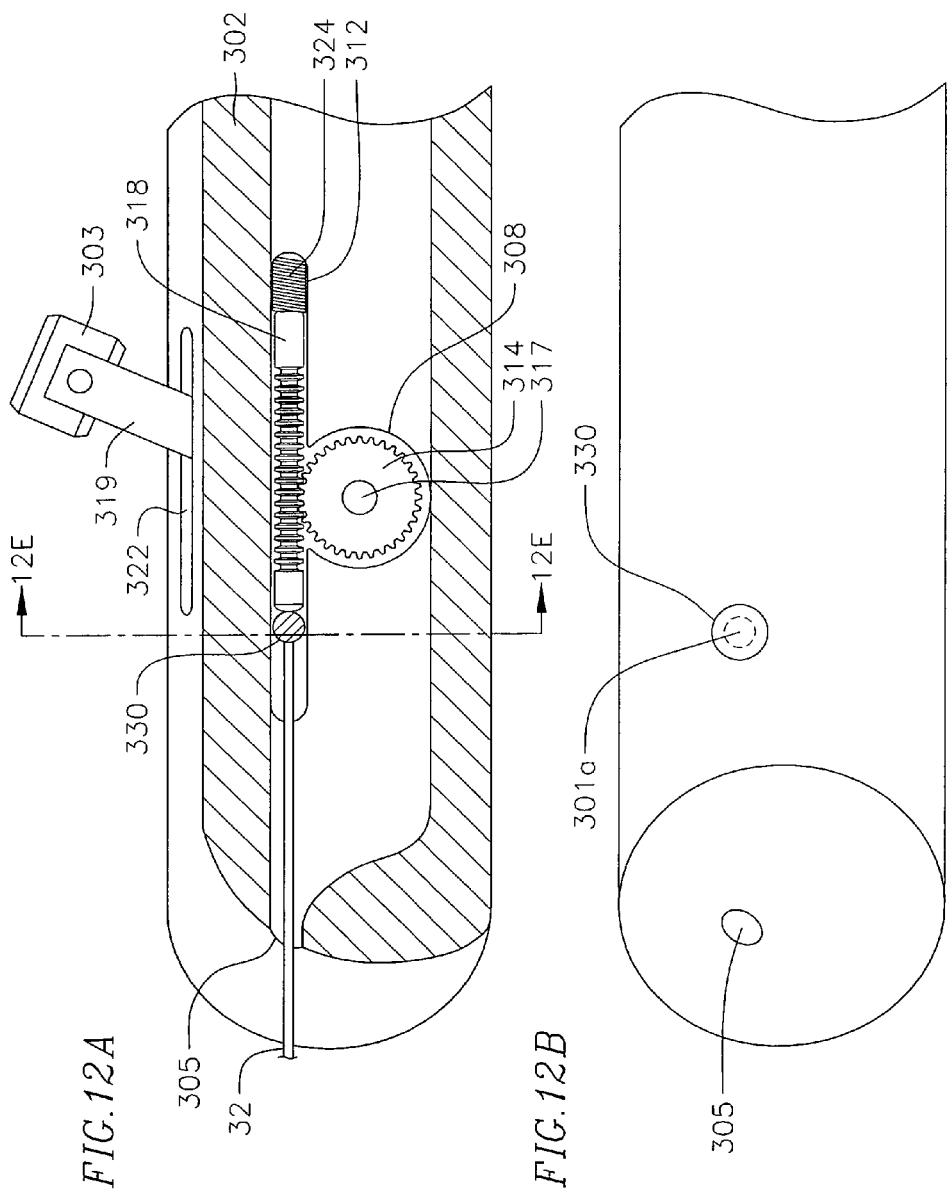
FIG. 12A is a cross-sectional view of the control handle of FIG. 8 including a locking mechanism according to one embodiment of the present invention.
FIG. 12B is an elevated side view of the control handle of FIG. 12A from an opposite direction.
Figures 12C, 12D:
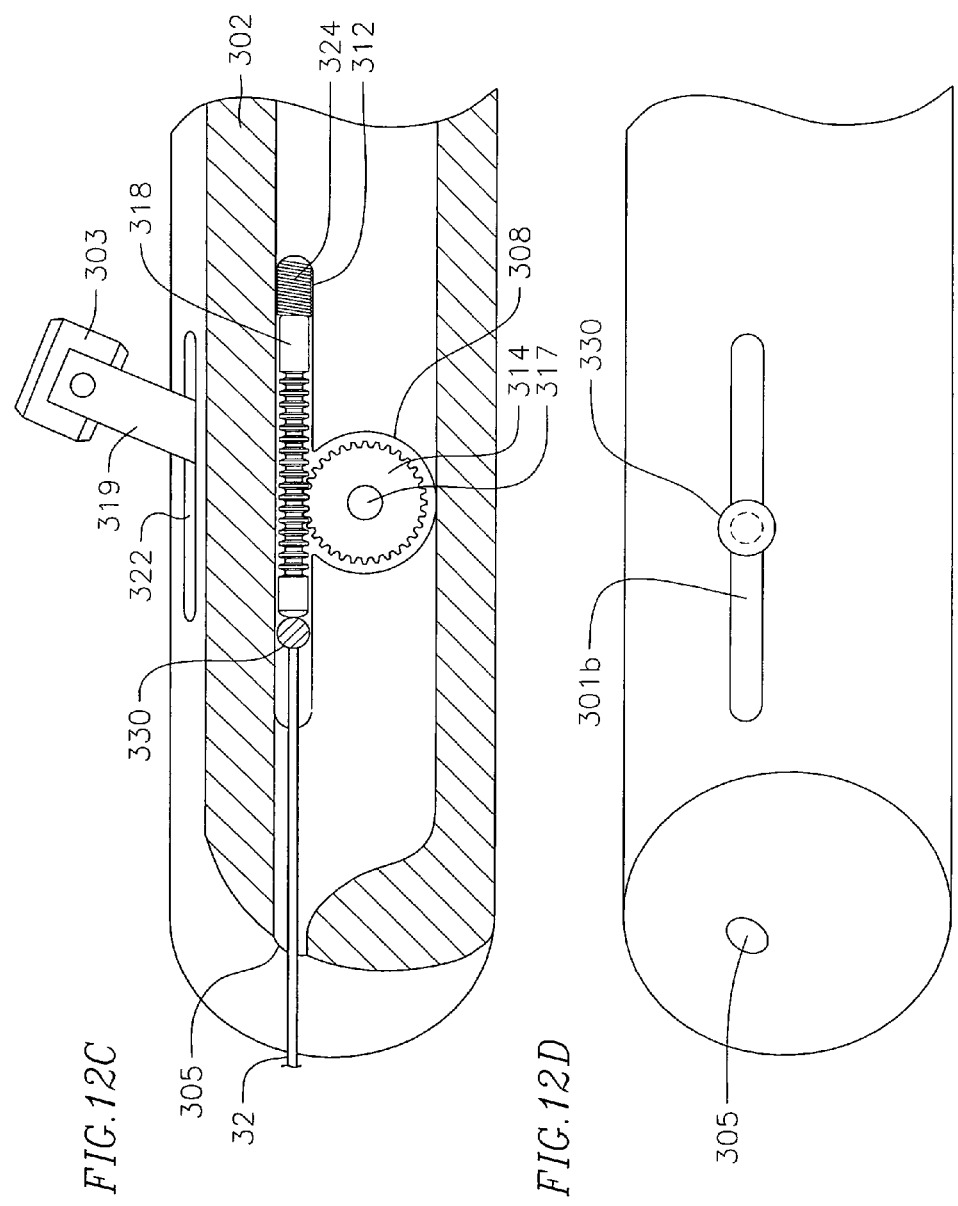
FIG. 12C is a cross-sectional view of the control handle of FIG. 8 including a locking mechanism according to another embodiment of the present invention.
FIG. 12D is an elevated side view of the control handle of FIG. 12C from an opposite direction.

For reasons discussed further below, the embodiment of the deflection means of FIG. 11 can also assume a configuration as shown in FIG. 11B, wherein the lever is pivoted distally. In particular, the spring 324 is stretched and the gear 314 is engaged with the carrier 318 at or near its proximal end which positions the distal end of the puller wire at a greater or maximum length distally from the distal end of the control handle in accommodating and allowing catheter deflection in the direction away from the puller wire moved distally. As discussed further below, this configuration of the deflection means in the embodiment of FIG. 11 is typically more the result of related proximal movement of the other puller wire in the pair of puller wires within the control handle.

As the catheter 10 of the present invention has a pair of puller wires 32a and 32b, a variety of bi-directional deflections are possible depending on factors that include the embodiment of the deflection means employed and where the distal end of the each puller wire is anchored. For example, where each of the deflection means of a puller wire pair within a control handle has an embodiment of FIG. 9, and the distal end of each puller wire is anchored a different distal distances X1 and X2 along the catheter, symmetrical "S" shape deflection (FIG. 15a) and asymmetrical "S" shape deflections (FIGS. 15b and 15c) are provided. In particular, the puller wire 32a may be actuated proximally followed by the puller wire 32b also being actuated proximally. By applying this sequence of lever movement in the control handle, the "S" shape deflection can be achieved with minimal, if any, distal movement of the nonactuated puller wire(s).

However, referring to FIG. 14 as another nonlimiting example, where each of the deflection means of a puller wire pair within a control handle has an embodiment of FIG. 11, and the distal end of each puller wire is anchored at generally the same distal distance Y1 and Y2 along the catheter, symmetrical bi-directional deflection is provided (see FIG. 16). In particular, deflection toward the puller wire 32a by proximal movement of the puller wire 32a effects a distal movement of the puller wire 32b. Similarly, deflection toward the puller wire 32b by proximal movement of the puller wire 32b effects a distal movement of the puller wire 32a. In that regard, the embodiment of the deflection means of FIGS. 11, 11A and 11B provide a resting or neutral position with both of the levers in a central position so that an operator can move a lever distally or proximally, which in turn can effect a reactive or accommodating proximal or distal movement in the other lever.

The foregoing examples are not intended to limit the different ways in which the deflection means can be configured or the different locations at which the distal end of the puller wires can be anchored. By providing a control handle with dual and generally independent levers for deflection, many types of bi-directional deflection are possible. Moreover, the dual lever control handle of the present invention can be adapted for use with a catheter body having a "lasso" type mapping assembly, such as described in U.S. Pat. No. 6,913,594, the entire disclosure of which is incorporated herein by reference. Therein, a first puller wire is provided for deflection of the intermediate section and a second puller wire is provided for contracting the mapping assembly. In addition, the control handles of the present invention can be used to activate a hinge by manipulation of the first puller wire, and to deflect the tip section by manipulation of the second puller wire. The control handle 16 of the present invention may further comprise locking mechanisms for locking each deflection means and mechanism in place once the desired degree of deflection has been accomplished. Any suitable mechanism can be used to temporarily maintain the desired position of the lever, the gear and/or the carrier. For example, as shown in FIGS. 12A-12E, the locking mechanism for a deflection means and mechanism comprises a set screw 330 extending from outside the handle housing 302 through a through hole 301a (FIGS. 12A and 12B) or a through slot 301b (FIGS. 12C and 12D) in the handle housing 302 into the channel 310. Once the desired degree of deflection has been accomplished, the set screw 330 is advanced into the corresponding channel 310 so that its end either extends across the channel and acts as a stop that blocks the distal end of the carrier or abuts and presses against the side of the carrier preventing movement of the carrier 318, thereby maintaining a constant degree of deflection.

Figure 13A:
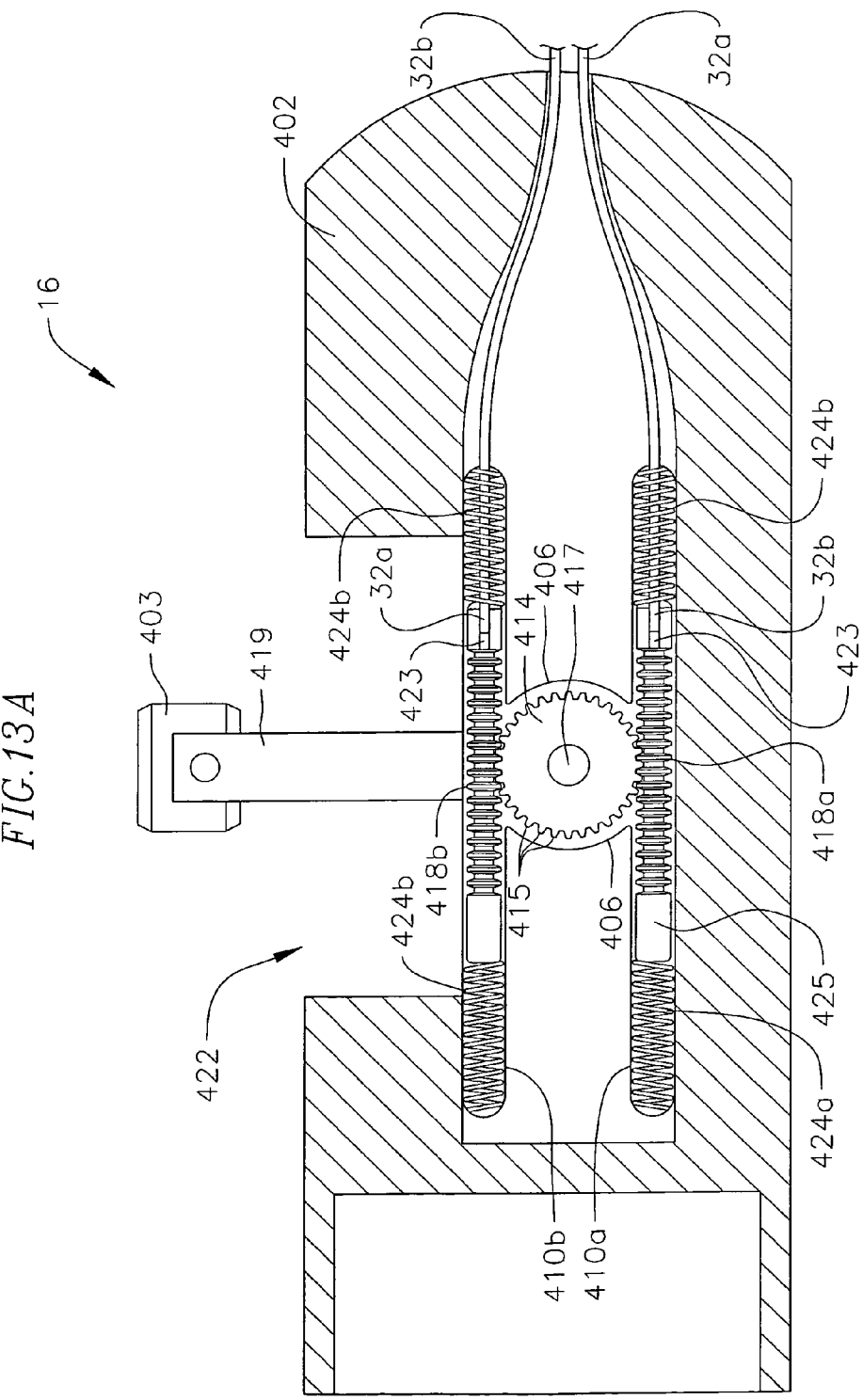
FIG. 13A is a side cross-sectional view of the handle of FIG. 13 taken along line 13-13.

With regard to any of the foregoing embodiments, to deflect the catheter, the user moves a desired thumb control 303 proximally. This proximal movement of the thumb control 303 causes the corresponding spur gear 314 to rotate. Upon rotation of the spur gear 314, the teeth 315 of the spur gear 314 engage the teeth or groove 321 of the corresponding carrier 318 resulting in proximal movement of the carrier 318, as shown in FIGS. 9A and 11A. The proximal movement of the carrier 318 causes compression of the spring 324 and creates tension in the corresponding puller wire 32, which draws the puller wire proximally, resulting in deflection of the tip section in the direction of the corresponding puller wire. Once the desired degree of deflection is achieved, the user advances the set screw 330 into the channel 310 to lock the carrier 318 against the bias of the spring 324 from return the carrier 318 to its resting or neutral position In yet another alternative embodiment, as shown in FIGS. 13 and 13A, the control handle 416 comprises a generally hollow, generally tubular handle housing 402 having a longitudinal axis and proximal and distal ends. The catheter body 12 is fixedly attached in a passage 405 at the distal end of the housing 402 by means of a glue joint and shrink sleeve as is known in the art. The puller wires 32a and 32b, lead wires 30 and any other wires, cables or tubes that extend through the catheter body extend through the passage 405 in the housing 402. The puller wires 32a and 32b proximal the passage 405 diverge slightly from each other toward their respective deflection means and mechanism for coupled manipulation of the puller wire pair by a single lever 419 having a thumb control 403. In the illustrated embodiment, the distal ends of the puller wires are anchored at a generally equal distal distance along the catheter from the distal end of the control handle.

In the housing 402, the deflection means and mechanism comprise means for converting rotational or pivotal movement into linear movement. In the illustrated embodiment, such means comprise a spur gear 414 in engagement with elongated carriers 418a and 418b at generally opposing ends of a diameter of the gear. Proximal end of each puller wire 32 is anchored to the distal end of a respective carrier 418. The spur gear 414 is rotationally coupled to the lever 419 by a pin 417. The lever 419 extends through a longitudinal slot 422 whose distal and proximal ends limit the distal and proximal positions of the lever. Accordingly, as an operator of the catheter 10 pivots the lever 419 by its thumb control 403 about the pin 417, the gear 414 rotates counterclockwise or clockwise, which in turn moves the carriers 318a and 318b in opposite directions. In particular, when the lever 419 is moved distally, the carrier 418b translates distally and the carrier 418a simultaneously translates proximally. And, when the lever 419 is moved proximally, the carrier 418b translates proximally and the carrier 418a simultaneously translates distally. The gear 414 may be, for example, a pinion, or a wormwheel, and the carrier 418 may be, for example, a rack with teeth that engages linear teeth of the pinion, or a worm with a spiral groove that engages angled teeth of the wormwheel. In any case, the gear 414 engages the carriers 418a and 418b such that upon rotation of the gear 314, a coupled, generally equal but opposite translations are effected in the carriers to advance one puller wire distally while drawing the other puller wire proximally. It is understood by one of ordinary skill in the art that depending on the desired ratio of rotation to translation between the gear and the carrier, one can vary various parameters and dimensions, including the diameter of the gear 414, the length of the toothed portion of the carriers 418a and 418b, and the size/plurality of the teeth of the gear and the carriers.

The handle housing 402 is configured with a generally circular cavity 406 to house the gear 414 and two generally elongated channel 410a and 410b to house the carriers. Opposing ends of the pin 417 are supported in the housing 402. The channels 410a and 410b are each configured and sized to guide its respective carrier to move in a longitudinal direction and prevent the carrier from disengaging the gear. The length of the channels 410 accommodates the distal and/or proximal movement of the carriers 418 as caused by the movement of the lever 419 by an operator of the catheter.

Each of the carriers can be biased toward a coupled "resting" position within the channels 410a and 410b by bias members 424A and 424B. In the illustrated embodiments, the bias members are springs whose distal ends are fixedly attached to the proximal ends of their respective carriers 418 and whose proximal ends are fixedly attached to the proximal end of their respective channels 310.

The embodiment of the deflection means depicted in FIG. 13A shows the lever 419 having a central position as it resting or neutral position, with no intended catheter deflection. The gear 414 is engaged with each carrier 418a and 418b at or near their longitudinal center which positions each anchored distal end of the puller wire at a mid-distance from the distal end of the control handle. As biased by the bias members 424, the lever 419 assumes or returns to this central position when not subjected to a force in the proximal or distal direction.

Depending on whether the catheter is to deflect toward the puller wire 32a or the puller wire 32b, the operator moves the thumb control 403 proximally or distally. In the illustrated embodiment, proximal movement of the thumb control deflects the tip section toward the puller wire 32a and distal movement of the thumb control deflects the tip section toward the puller wire 32b. Once the desired deflection is achieved, the operator may advance a set screw into one or each of the channels 410 to temporarily lock the deflection means in place.

The preceding description has been presented with reference to certain exemplary embodiments of the invention. Workers skilled in the art and technology to which this invention pertains will appreciate that alterations and changes to the described structures may be practiced without meaningfully departing from the principal, spirit and scope of this invention. Accordingly, the foregoing description should not be read as pertaining only to the precise structures described and illustrated in the accompanying drawings, but rather should be read consistent with and as support for the following claims which are to have their fullest and fairest scope.

What is claimed is:

1. A bi-directional catheter comprising:
   an elongated catheter body having proximal and distal ends;
   a tip section comprising a flexible tubing having proximal and distal ends and first and second off axis lumens extending therethrough, the tip section being distal the catheter body and configured for bi-directional deflection in a first direction and a second direction generally opposite the first direction;
   a control handle mounted to the proximal end of the catheter body;
   a first puller wire extending through the first lumen and a second puller wire extending through the second lumen;
   wherein the control handle comprises:
      a first deflection mechanism comprising:
         a first lever adapted for translational movement by an operator;
         a first gear in engagement with a first carrier that is connected to a proximal end of the first puller wire, wherein the first gear is rotatably coupled to the first lever and drives the first carrier distally or proximally in response to rotation of the first gear by the first lever for deflecting the tip section in the first direction, the first carrier riding in a first dedicated channel having a first proximal wall and a first distal wall; and
         a first biasing member configured to act directly on the first carrier to bias the first lever toward a resting position, wherein the first biasing member is either fixedly attached to the first proximal wall of the first dedicated channel and a proximal end of the first carrier or fixedly attached to the first distal wall of the first dedicated channel and a distal end of the first carrier; and
      a second deflection mechanism comprising:
         a second lever adapted for translational movement by an operator;

a second gear in engagement with a second carrier that is connected to a proximal end of the second puller wire, wherein the second gear is rotatably coupled to the second lever and drives the second carrier distally or proximally in response to rotation of the second gear by the second lever for deflecting the tip section in the second direction, the second carrier riding in a second dedicated channel having a second proximal wall and a second distal wall; and a second biasing member configured to act directly on the second carrier to bias the second lever toward a resting position, wherein the second biasing member is either fixedly attached to the second proximal wall of the second dedicated channel and a proximal end of the second carrier or fixedly attached to the second distal wall of the second dedicated channel and a distal end of the second carrier.

2. A catheter of claim 1, wherein each of the first and second gears comprises a pinion and each of the first and second carriers comprises a rack.

3. A catheter of claim 1, wherein each of the first and second gears comprises a wormwheel and each of the first and second carriers comprises a worm.

4. A catheter of claim 1, wherein distal ends of the first and second puller wires are anchored at different distal distances from the control handle.

5. A catheter of claim 1, wherein distal ends of the first and second puller wires are anchored at generally equal distal distances from the control handle.

6. A catheter of claim 1, wherein each of the first and second levers is adapted for both distal and proximal movement from the resting position.

7. A catheter of claim 1, wherein each of the first and second levers is adapted for only proximal movement from the resting position and distal movement toward the resting position.

8. A catheter of claim 1, wherein the bi-directional deflection comprises symmetrical bi-directional deflection.

9. A catheter of claim 1, wherein the bi-directional deflection comprises asymmetrical "S" shape deflection.

10. A catheter of claim 1, wherein the bi-directional deflection comprises symmetrical "S" shape deflection.

11. The catheter according to claim 1, whereby proximal movement of the first carrier of the control handle results in deflection of the tip section in the first direction corresponding to a direction of the first lumen in the tip section in which the first puller wire is anchored.

12. The catheter according to claim 1, whereby proximal movement of the second carrier of the control handle results in deflection of the tip section in the second direction corresponding to a direction of the second lumen in the tip section in which the second puller wire is anchored.

* * * * *